(12) United States Patent
Wischhusen et al.

(10) Patent No.: US 10,781,251 B2
(45) Date of Patent: *Sep. 22, 2020

(54) MONOCLONAL ANTIBODIES TO GROWTH AND DIFFERENTIATION FACTOR 15 (GDF-15)

(71) Applicant: JULIUS-MAXIMILLIANS-UNIVERSITÄT WÜRZBURG, Würzburg (DE)

(72) Inventors: Jörg Wischhusen, Würzburg (DE); Markus Junker, Würzburg (DE); Thomas Müller, Veitshöchheim (DE); Stefan Saremba, Würzburg (DE)

(73) Assignee: JULIUS-MAXIMILIANS-UNIVERSITÄT WÜRZBURG, Würzburg (DE)

( * ) Notice: Subject to any disclaimer, the term of this patent is extended or adjusted under 35 U.S.C. 154(b) by 78 days.

This patent is subject to a terminal disclaimer.

(21) Appl. No.: 15/918,841

(22) Filed: Mar. 12, 2018

(65) Prior Publication Data
US 2018/0305447 A1 Oct. 25, 2018

Related U.S. Application Data

(63) Continuation of application No. 14/431,281, filed as application No. PCT/EP2013/070127 on Sep. 26, 2013, now abandoned.

(30) Foreign Application Priority Data

Sep. 26, 2012 (EP) .................... 12186185

(51) Int. Cl.
*C07K 16/22* (2006.01)
*A61K 45/06* (2006.01)
*A61K 39/00* (2006.01)

(52) U.S. Cl.
CPC .............. *C07K 16/22* (2013.01); *A61K 45/06* (2013.01); *A61K 2039/505* (2013.01); *C07K 2317/34* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 8,003,099 | B2 | 8/2011 | Auer et al. |
| 2001/0010908 | A1 | 8/2001 | Billing-Medel et al. |
| 2002/0052480 | A1 | 5/2002 | Park et al. |
| 2006/0148709 | A1 | 7/2006 | Unsicker et al. |
| 2007/0180543 | A1 | 8/2007 | Eling et al. |
| 2009/0004181 | A1 | 1/2009 | Breit |
| 2009/0324604 | A1 | 12/2009 | Liu et al. |
| 2010/0278843 | A1 | 11/2010 | Breit et al. |
| 2011/0262444 | A1 | 10/2011 | Hyesook |
| 2014/0193427 | A1 | 7/2014 | Lerner et al. |
| 2014/0378665 | A1 | 12/2014 | Xiong et al. |

FOREIGN PATENT DOCUMENTS

| CN | 102321173 A | 1/2012 |
| EP | 2 681 308 B1 | 3/2015 |
| WO | 2005/099746 A1 | 10/2005 |
| WO | 2009/021293 A1 | 2/2009 |
| WO | 2011/050407 A1 | 5/2011 |
| WO | 2013/023557 A1 | 2/2013 |
| WO | 2014/100689 A1 | 6/2014 |

OTHER PUBLICATIONS

Paul, Fundamental Immunology, Raven Press, New York, 1993, pp. 292-295.*
Casset et al. (Biochem Biophys Res Comm. 2003; 307:198-205).*
MacCallum et al. (J Mol Biol. 1996; 262:732-745).*
Vajdos et al. (J Mol Biol. 2002; 320(2):415-428).*
Holm et al. (Mol Immunol. 2007; 44(6):1075-1084).*
Chen et al. (J Mol Biol. 1999; 293:865-881).*
https://www.uniprot.org/uniprot/Q99988; accessed Nov. 12, 2019.*
Griner et al. (2013, Biochem. Pharmacol. 85(1):46-58).*
Sadasivan et al. (2018, Cancer Res 78(13 Suppl): Abstract nr. 4211).*
Weide et al. (2016, J Invest Dermatol 136:2444-2452).*
Gkretsi et al. (2020, Anticancer Research 40:1375-1385).*
Zimmers et al. (2008, J Cancer Res Clin Oncol 134:753-759).*
Zimmers et al. (2010, J Cancer Res Clin Oncol 136:571-576).*
Husaini et al. (2015, PLoS ONE 10(2):e0115189).*
Wang et al. (2013, Biochemical Pharmacology 85:597-606).*
Gura (Science, v278, 1997, pp. 1041-1042).*
Freshney (Culture of Animal Cells, a Manual of Basic Technique, Alan R. Liss, Inc., 1983, New York, p. 4).*
Dermer (Bio/Technology, 1994, 12:320).*
Zips et al. (2005, In Vivo 19:1-8).*
2013, Nature Biotechnology 31:85.*
U.S. Appl. No. 14/431,281 2015-0239968 A1, filed Mar. 25, 2015, Aug. 27, 2015, Wischhusen.
Bauskin, Asne. R. et al., (2005) "The Propeptide Mediates Formation of Stromal Stores of PROMIC-1: Role in Determining Prostrate Cancer Outcome," Cancer Res: vol. 65, No. 6, pp. 2330-2336.
Boyle, G. et al., (2009) "Macrophage Inhibitory Cytokine-1 Is Overexpressed in Malignant Melanoma and is Associated with Tumorigenicity." Journal of Investigative Dermatology vol. 129, pp. 383-391.
Brown, D.A. et al., (2009) "Macrophage Inhibitory Cytokine 1: A New Prognostic Marker in Prostate Cancer." Clin. Cancer Res., vol. 15, No. 21, pp. 6658-6664.

(Continued)

*Primary Examiner* — Elizabeth C. Kemmerer
(74) *Attorney, Agent, or Firm* — Lathrop GPM LLP; Andrew T. Wilkins; Rebecca Wright

(57) ABSTRACT

The present invention relates to novel monoclonal anti-human-GDF-15 antibodies, pharmaceutical compositions, kits, methods and uses and the cell lines capable of producing the monoclonal antibodies described herein. The present invention further relates to novel antibodies to human GDF-15 capable of inhibiting cancer growth.

20 Claims, 4 Drawing Sheets
Specification includes a Sequence Listing.

(56) References Cited

OTHER PUBLICATIONS

Chen et al., (1999) "Selection and Analysis of an Optimized Anti-VEGF Antibody: Crystal Structure of an Affinity-matured Fab in Complex with Antigen." J. Mol. Biol., 293, pp. 865-881.
Chen, S. J. et al., (2007) "Prostate-Derived Factor as a Paracrine and Autocrine Factor for the Proliferation of Androgen Receptor-Positive Human Prostate Cancer Cells." The Prostate, vol. 67, pp. 557-571.
Chothia and Lesk, (1987) "Canonical Structures for the Hypervariable Regions of Immunoglobulins," J. Mol. Biol. 196, pp. 901-917.
Chothia, C et al. (1989) "Conformations of immunoglobulin hypervariable regions." Nature, vol. 342 (6252), pp. 877-883.
Clackson, T. et al. (1991) "Making antibody fragments using phage display libraries." Nature. vol. 352 (6336), pp. 624-628.
De Pascalis et al., (2002) "Grafting of 'Abbreviated' Complementarity-Determining Regions Containing Specificity-Determining Residues Essential for Ligand Contact to Engineer a Less Immunogenic Humanized Monoclonal Antibody." The Journal of Immunology, 169(6): pp. 3076-3084.
Fairlie, W. Douglas et al., (2001) "Epitope Mapping of the Transforming Growth Factor-[beta] Superfamly Protein, Macrophage Inhibitory Cytokine-1 (MIC-1): Identification of at Least Five Distinct Epitope Specificites", Biochemistry, vol. 40, No. 1, pp. 65-73.
Fairlie, W. Douglas et al., (1999) "MIC-1 is a novel TGF-beta superfamily cytokine associated with macrophage activation." Journal of Leukocyte Biology, vol. 65, pp. 2-5.
Fairlie, W. et al. (2000) "Expression of a TGF-beta superfamily protein, macrophage inhibitory cytokine-1, in the yeast *Pichia pastoris*," Gene. 254:67-76.
Ghahroudi, Arbabi M. et al.: (1997) "Selection and identification of single domain antibody fragments from camel heavy-chain antibodies." FEBS Lett. vol. 414 No. 3, pp. 521-526.
Giudicelli, V. et al. (2004) "IMGT/V-QUEST, an integrated software program for immunoglobulin and T cell receptor V-J and V-D-J rearrangement analysis". Nucleic Acids Res vol. 32 (Web Server issue):W435-40.
Hollinger, P. et al. (1993) ""Diabodies": small bivalent and bispecific antibody fragments." Proc Natl Acad Sci USA. vol. 90(14): pp. 6444-6448.
Holt, L.J. et al. (2003) "Domain antibodies: proteins for therapy." Trends Biotechnol., vol. 21(11): pp. 484-490.
Huang, C-Y and Qian, David Z. et al., (2009) "Prostate Cancer-Associated Gene Expressions Alterations Determined from Needle Biopsies." Clin. Cancer Res., vol. 15, No. 9, pp. 3135-3142.
Huang, C-Y et al. (2007) "Molecular alterations in prostate carcinomas that associate with in vivo exposure to chemotherapy: identification of a cytoprotective mechanism involving growth differentiation factor 15." Clin Cancer Res. vol. 13(19): pp. 5825-5833.
Janeway et al., Immunobiology: The Immune System in Health and Disease. 5th Ed., New York, Garland Science (2001).
Johnen, H. et al. (2007) "Tumor-induced anorexia and weight loss are mediated by the TGF-beta superfamily cytokine MIC-1," Nature Medicine. 13(11):1333-1340.
Jones, P.T. et al. (1986) "Replacing the complementarity-determining regions in a human antibody with those from a mouse." Nature. vol. 321(6069): pp. 522-525.
Kempf, T. et al., (2011) "GDF-15 is an inhibitor of leukocyte integrin activation required for survival after myocardial infarction in mice." Nature Medicine, vol. 17, No. 5, pp. 581-589.
Kohler G and Milstein C (1975) "Continuous cultures of fused cells secreting antibody of predefined specificity." Nature. vol. 256(5517): pp. 495-497.
Liu, T. et al., (2003) "Macrophage Inhibitory Cytokine 1 Reduces Cell Adhesion and induces Apoptosis in Prostate Cancer Cells." Cancer Research, vol. 63, pp. 5034-5040.

MacCallum et al., (1996) "Antibody-antigen Interactions: Contact Analysis and Binding Site Topography." J. Mol. Biol., 262, pp. 732-745.
Marks, J.D. et al., (1991) "By-passing immunization. Human antibodies from V-gene libraries displayed on phage." J Mol. Biol. vol. 222(3): pp. 581-597.
Mimeault, M. and Batra, S.K., (2010) "Divergent Molecular Mechanisms Underlying the Pleiotropic Functions of Macrophage Inhibitory Cytokine-1 in Cancer." J. Cell. Physiol., vol. 224, No. 3, pp. 626-635.
Park, J.Y. et al., (2008) "Expression of nonsteroidal anti-inflammatory drug-activated gene-1 (NAG-1) inversely correlates with tumor progression in gastric adenomas and carcinomas." J. Cancer Res. Clin. Oncol., vol. 134, pp. 1029-1035.
Riechmann L et al., (1988) "Reshaping human antibodies for therapy." Nature. vol. 332(6162): pp. 323-327.
Roth, P. et al., (2010) "GDF-15 Contributes to Proliferation and Immune Escape of Malignant Gliomas." Clin. Cancer Res., vol. 16, No. 15, pp. 3851-3859.
Rudikoff et al., (1982) "Single amino acid substitution altering antigen-binding specificity." PNAS USA, 79, pp. 1979-1983.
Saerens D et al., (2008) "Single-domain antibodies as building blocks for novel therapeutics." Curr Opin Pharmacol. vol. 8 (5): pp. 600-608.
Siegel D.L., (2002) "Recombinant monoclonal antibody technology." Transfus Clin Biol., vol. 9(1):15-22.
Stefanescu, Raluca et al., (2007) "Mass spectometric approaches for elucidation of antigen-antibody recognition structures in molecular immunology." Eur. J. Mass Spectrom., vol. 13, pp. 69-75.
Suckau, Detlev et al., (1990) "Molecular epitope identification by limited proteolysis of an immobilized antigen-antibody complex and mass spectormetric peptide mapping." Proc. Natl. Acad. Sci. USA, vol. 87, pp. 9848-9852.
Tanno et al., (2010) "Growth differentiation factor 15 in erythroid health and disease." Curr Opin Hematol. 17(3): 184-190.
Tanno, T. et al., (2011) "The TGF-beta Family Member Growth Differntiation Factor 15 (GDF 15) Regula Self-Renewal of Multiple Myeloma Cancer Stem Cells," Blood, 118(21):2954.
Vajdos et al., (2002) "Comprehensive Functional Maps of the Antigen-binding Site of an Anti-ErbB2 Antibody Obtained with Shotgun Scanning Mutagenesis." J. Mol. Biol., 320, pp. 415-428.
Wang, Z. et al., (2000) "Universal PCR amplification of mouse immunoglobulin gene variable regions: the design of degenerate primers and an assessment of the effect of DNA polymerase 3' to 5' exonuclease activity." Journal of Immunological Methods, vol. 233, pp. 167-177.
Wu et al., (1999) "Humanization of a Murine Monoclonal Antibody by Simultaneous Optimization of Framework and CDR Residues." J. Mol. Biol., 294, pp. 151-162.
Zhan, Feng, (2011) "The Preparation and Functional Characterization of an Anti-GDF15 Monoclonal Antibody," Chinese Master's These Full-Text Database, Mdeicine and Health Sciences (Abstract).
Culang et al. (2013) "The structural basis of antibody-antigen recognition," Frontiers in Immunology, vol. 4, Article 302, 13 pp.
Abd El-Aziz et al. "Cleavage of growth differentiation factor 15 (GDF15) by membrane type 1-matrix metalloproteinase abrogates GDF15-mediated suppression of tumor cell growth", Cancer Sci., Sep. 2007, vol. 98, No. 9, pp. 1330-1335.
Baek et al. "Upregulation and secretion of macrophage inhibitory cytokine-1 (MIC-1) in gastric cancers", Clinica Chimica Acta, 2009, vol. 401, pp. 128-133, doi: 10.1016/j.cca.2008.12.008.
Baek et al., "Nonsteroidal Anti-Inflammatory Drug-Activated Gene-1 Over Expression in Transgenic Mice Suppresses Intestinal Neoplasia", Gastroenterology, 2006, vol. 131, pp. 1553-1560.
Bauskin et al., "The TGF-ß Superfamily Cytokine MIC-1/GDF15: Secretory Mechanisms Facilitate Creation of Latent Stromal Stores", Journal of Interferon & Cytokine Research, 2010, vol. 30, No. 6, pp. 27-35.
Blanco-Calvo et al., "Circulating levels of GDF15, MMP7 and miR-200c as a poor prognostic signature in gastric cancer", Future Oncology, 2014, vol. 10, No. 7, pp. 1187-1202.

(56) References Cited

OTHER PUBLICATIONS

Bootcov et a., "MIC-1, a novel macrophage inhibitory cytokine. Is a divergent member of the TGF-ß superfamily", Proc. Nat'l. Acad. Sci., Oct. 1997, vol. 94, pp. 11514-11519.

Boyle et al., "Macrophage Inhibitory Cytokine-1 Is Overexpressed in Malignant Melanoma and Is Associated with Tumorigenicity", Aug. 28, 2008, vol. 129, pp. 383-391, doi: 10.1038/jid.2008.270.

Brown et al., "MIC-1 Serum Level and Genotype: Associations with Progress and Prognosis of Colorectal Carcinoma", Clinical Cancer Research, Jul. 2003, vol. 9, pp. 2642-2650.

Bruzzese et al., "Local and Systemic Protumorigenic Effects of Cancer-Associated Fibroblast-Derived GDF15", Cancer Research, Apr. 29, 2014, vol. 74, No. 13, pp. 3408-3418, doi: 10.1158/0008-5472.CAN-13-2259.

Corre et al., "Bioactivity and Prognostic Significance of Growth Differentiation Factor GDF15 Secreted by Bone Marrow Mesenchymal Stem Cells in Multiple Myeloma", Cancer Research, Feb. 2, 2012, vol. 72, No. 6, pp. 1395-1407, doi: 10.1158/0008-5472.CAN-11-0188.

Fisher et al., "MIC-1/GDF15 in Barrett's oesophagus and oesophageal adenocarcinoma", British Journal of Cancer, 2015, vol. 112, pp. 1384-1391, doi: 10.1038/bjc.2015.100.

Galon et al., "Type, Density, and Location of Immune Cells Within Human Colorectal Tumors Predict Clinical Outcome", Science Mag., Sep. 29, 2006, vol. 313, pp. 1960-1993.

Griner et al., "Growth differentiation factor 15 stimulates rapamycin-sensitive ovarian cancer cell growth and invasion", Biochemical Pharmacology, vol. 85, pp. 46-58.

Huh et al., "Macrophage Inhibitory Cytokine-1 Regulates Melanoma Vascular Development", The American Journal of Pathology, Jun. 2010, vol. 176, No. 6, pp. 2948-2957.

Husaini et al., "Macrophage Inhibitory Cytokine-1 (MIC-1/GDF15) Slows Cancer Development but Increases Metastases in TRAMP Prostate Cancer Prone Mice", PLOS ONE, Aug. 2012, vol. 7, No. 8, pp. 1-9.

Ji et al., "Twist promotes invasion and cisplatin resistance in pancreatic cancer cells through growth differentiation factor 15", Molecular Medicine Reports, 2015, vol. 12, pp. 3841-3848.

Jones et al., "Supraphysiologic Administration of GDF11 Induces Cachexia in Part by Upregulating GDF15", Cell Reports, 2018, vol. 22, pp. 1522-1530.

Joshi et al., "Growth differentiation factor 15 (GDF15)-mediated HER2 phosphorylation reduces trastuzumab sensitivity of HER2-overexpressing breast cancer cells", Biochemical Pharmacology, 2011, vol. 82, pp. 1090-1099.

Kang et al., "Tolfenamic Acid Induces Apoptosis and Growth Inhibition in Head and Neck Cancer: Involvement of NAG-1 Expression", PLOS ONE, Apr. 2012, vol. 7, No. 4, pp. 1-10.

Kim et al., "Implication of NAG-1 in synergistic induction of apoptosis by combined treatment of sodium salicylate and PI3K/MEK1/2 inhibitors in A549 human lung adenocarcinoma cells", Biochemical Pharmacology, 2008, vol. 75, pp. 1751-1760.

Kim et al., "Macrophage inhibitory cytokine-1 activates AKT and ERK-1/2 via the transactivation of ErbB2 in human breast and gastric cancer cells", Carcinogenesis, 2008, vol. 29, No. 4, pp. 704-712.

Kim et al., "NSAID-activated gene 1 mediates pro-inflammatory signaling activation and paclitaxel chemoresistance in type I human epithelial ovarian cancer stem-like cells", Oncotarget, Sep. 30, 2016, vol. 7, No. 44, pp. 72148-72166.

Li et al., "GDF15 promotes EMT and metastasis in colorectal cancer", Oncotarget, Oct. 22, 2015, vol. 7, No. 1, pp. 860-872.

Li et al., "Growth differentiation factor 15 is a promising diagnostic and prognostic biomarker in colorectal cancer", J. Cell. Mol. Med., 2016, vol. 20, No. 8, pp. 1420-1426.

Liu et al., "Association of Serum Level Growth Differentiation Factor 15 with Liver Cirrhosis and Hepatocellular Carcinoma", PLOS ONE, May 21, 2015, vol. 10, No. 5, pp. 1-13.

Mehta et al., "A Prospective Study of Macrophage Inhibitory Cytokine-1 (MIC-1/GDF15) and Risk of Colorectal Cancer", JNCI, Apr. 9, 2014, vol. 106, No. 4, pp. 1-8.

Mehta et al., "Association Between Plasma Levels of Macrophage Inhibitory Cytokine-1 Before Diagnosis of Colorectal Cancer and Mortality", Gastroenterology, 2015, vol. 149, pp. 614-622.

Patel et al., "GDF15 Provides an Endocrine Signal of Nutritional Stress in Mice and Humans", Cell Metabolism, 2019, vol. 29+, pp. 707-718.

Roth et al., "GDF-15 Contributes to Proliferation and Immune Escape of Malignant Glinomas", Clinical Cancer Research, Jun. 9, 2010, vol. 16, pp. 3851-3860.

Schiegnitz, et al., "GDF 15 as an anti-apoptotic, diagnostic and prognostic marker in oral squamous cell carcinoma", Oral Oncology, 2012, vol. 48, pp. 608-614.

Schiegnitz, et al., "Growth differentiation factor 15 as a radiation-induced marker in oral carcinoma increasing radiation resistance", Journal of Oral Pathology and Medicine, 2016, vol. 45, pp. 63-69.

Selander et al., "Serum Macrophage Inhibitory Cytokine-1 Concentrations Correlate with the Presence of Prostate Cancer", Cancer Epidemiology, Biomarkers & Prevention, Mar. 2007, vol. 16, No. 3, 532-537.

Senapati et al., "Overexpression of macrophage inhibitory cytokine-1 induces metastasis of human prostate cancer cells through the FAK-RhoA signaling pathway", Oncogene, 2010, vol. 29, pp. 1293-1302.

Senovilla et al., "Prognostic and predictive value of the immune infiltrate in cancer", Trial Watch, OncoImmunology, 2012, vol. 1, No. 8, pp. 1323-1343.

Shnaper et al., "Elevated levels of MIC-1/GDF15 in the cerebrospinal fluid of patients are associated with glioblastoma and worse outcome", Int. J. Cancer, 2009, vol. 125, pp. 2624-2630.

Staff et al., "Elevated Plasma Growth Differentiation Factor-15 Correlates with Lymph Node Metastases and Poor Survival in Endometrial Cancer", Clinical Cancer Research, Jul. 15, 2011, vol. 17, No. 14, pp. 4825-4833.

Staff et al., "Growth differentiation factor-15 as a prognostic biomarker in ovarian cancer", Gynecologic Oncology, 2010, vol. 118, pp. 237-243.

Tanno et al., "Growth differentiating factor 15 enhances the tumor-initiating and self-renewal potential of multiple myeloma cells", Blood, Jan. 30, 2014, vol. 123, No. 5, pp. 725-733.

Tsui et al., "Growth differentiation factor-15 upregulates interleukin-6 to promote tumorigenesis of prostate carcinoma PC-3 cells", Journal of Molecular Endocrinology, 2012, vol. 49, pp. 153-163.

Wang et al., "The H6D genetic variation of GDF15 is associated with genesis, progress, and prognosis in colorectal cancer", Pathology—Research and Practice, 2015, vol. 211, pp. 845-850.

Westhrin et al., "Growth differentiation factor 15 (GDF15) promotes osteoclast differentiation and inhibits osteoblast differentiation and high serum GDF15 levels are associated with multiple myeloma bone disease", haematologica, 2015, vol. 100, pp. 511-514.

Xu et al., "Growth differentiation factor 15 induces growth and metastasis of human liver cancer stem-like cells via AKT/GSK-3ß/ß-catenin signaling", Oncotarget, 2017, vol. 8, No. 10, pp. 16972-16987.

Yang et al., "Elevated level of serum growth differentiation factor 15 is associated with oral leukoplakia and oral squamous cell carcinoma", Journal of Oral Pathology and Medicine, 2014, vol. 43, pp. 28-34.

Yang et al., "Gdf 15 is a potential predictive biomarker for TPF induction chemotherapy and promotes tumorigenesis and progression in oral squamous cell carcinoma", Annals of Oncology, 2014, vol. 25, pp. 1215-1222.

* cited by examiner

SEQUENCE LISTING

```
<160> NUMBER OF SEQ ID NOS: 26

<210> SEQ ID NO 1
<211> LENGTH: 97
<212> TYPE: PRT
<213> ORGANISM: Mus musculus

<400> SEQUENCE: 1

Gln Val Lys Leu Gln Gln Ser Gly Pro Gly Ile Leu Gln Ser Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Thr
    50                  55                  60

Leu Lys Ser Arg Leu Thr Ile Ser Lys Asp Pro Ser Arg Asn Gln Val
65                  70                  75                  80

Phe Leu Lys Ile Thr Ser Val Asp Thr Ala Asp Thr Ala Thr Tyr Tyr
                85                  90                  95

Cys
```

<210> SEQ ID NO 2
<211> LENGTH: 88
<212> TYPE: PRT
<213> ORGANISM: Mus musculus

<400> SEQUENCE: 2

Asp Ile Val Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Phe Leu Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys
                85

<210> SEQ ID NO 3
<211> LENGTH: 10
<212> TYPE: PRT
<213> ORGANISM: Mus musculus

<400> SEQUENCE: 3

Gly Phe Ser Leu Ser Thr Ser Gly Met Gly
1               5                   10

<210> SEQ ID NO 4
<211> LENGTH: 7
<212> TYPE: PRT
<213> ORGANISM: Mus musculus

<400> SEQUENCE: 4

Ile Tyr Trp Asp Asp Asp Lys
1               5

<210> SEQ ID NO 5
<211> LENGTH: 10
<212> TYPE: PRT
<213> ORGANISM: Mus musculus

<400> SEQUENCE: 5

Ala Arg Ser Ser Tyr Gly Ala Met Asp Tyr
1               5                   10

<210> SEQ ID NO 6
<211> LENGTH: 6
<212> TYPE: PRT
<213> ORGANISM: Mus musculus

<400> SEQUENCE: 6

Gln Asn Val Gly Thr Asn
1               5

<210> SEQ ID NO 7
<211> LENGTH: 9
<212> TYPE: PRT
<213> ORGANISM: Mus musculus

<400> SEQUENCE: 7

Gln Gln Tyr Asn Asn Phe Pro Tyr Thr
1               5

<210> SEQ ID NO 8
<211> LENGTH: 114
<212> TYPE: PRT
<213> ORGANISM: Artificial Sequence
<220> FEATURE:
<223> OTHER INFORMATION: recombinant mature human GDF-15 protein

<400> SEQUENCE: 8

Gly Ser Ala Arg Asn Gly Asp His Cys Pro Leu Gly Pro Gly Arg Cys
1               5                   10                  15

Cys Arg Leu His Thr Val Arg Ala Ser Leu Glu Asp Leu Gly Trp Ala
            20                  25                  30

Asp Trp Val Leu Ser Pro Arg Glu Val Gln Val Thr Met Cys Ile Gly
        35                  40                  45

Ala Cys Pro Ser Gln Phe Arg Ala Ala Asn Met His Ala Gln Ile Lys
    50                  55                  60

Thr Ser Leu His Arg Leu Lys Pro Asp Thr Val Pro Ala Pro Cys Cys
65                  70                  75                  80

Val Pro Ala Ser Tyr Asn Pro Met Val Leu Ile Gln Lys Thr Asp Thr
                85                  90                  95

Gly Val Ser Leu Gln Thr Tyr Asp Asp Leu Leu Ala Lys Asp Cys His
            100                 105                 110

Cys Ile

<210> SEQ ID NO 9
<211> LENGTH: 308
<212> TYPE: PRT
<213> ORGANISM: Homo sapiens

<400> SEQUENCE: 9

Met Pro Gly Gln Glu Leu Arg Thr Val Asn Gly Ser Gln Met Leu Leu
1               5                   10                  15

Val Leu Leu Val Leu Ser Trp Leu Pro His Gly Gly Ala Leu Ser Leu
            20                  25                  30

Ala Glu Ala Ser Arg Ala Ser Phe Pro Gly Pro Ser Glu Leu His Ser
        35                  40                  45

Glu Asp Ser Arg Phe Arg Glu Leu Arg Lys Arg Tyr Glu Asp Leu Leu
    50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
        115                 120                 125

Pro Thr Ala Ser Arg Ser Trp Asp Val Thr Arg Pro Leu Arg Arg Gln
    130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

```
Arg Arg Ala Arg Ala Arg Asn Gly Asp His Cys Pro Leu Gly Pro Gly
        195                 200                 205

Arg Cys Cys Arg Leu His Thr Val Arg Ala Ser Leu Glu Asp Leu Gly
210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
        260                 265                 270

Cys Cys Val Pro Ala Ser Tyr Asn Pro Met Val Leu Ile Gln Lys Thr
        275                 280                 285

Asp Thr Gly Val Ser Leu Gln Thr Tyr Asp Asp Leu Leu Ala Lys Asp
        290                 295                 300

Cys His Cys Ile
305

<210> SEQ ID NO 10
<211> LENGTH: 322
<212> TYPE: PRT
<213> ORGANISM: Artificial Sequence
<220> FEATURE:
<223> OTHER INFORMATION: human GDF-15 precursor protein + N-terminal and
      C-terminal GSGS linker

<400> SEQUENCE: 10

Gly Ser Gly Ser Gly Ser Met Pro Gly Gln Glu Leu Arg Thr Val
1               5                   10                  15

Asn Gly Ser Gln Met Leu Leu Val Leu Leu Val Leu Ser Trp Leu Pro
                20                  25                  30

His Gly Gly Ala Leu Ser Leu Ala Glu Ala Ser Arg Ala Ser Phe Pro
            35                  40                  45

Gly Pro Ser Glu Leu His Ser Glu Asp Ser Arg Phe Arg Glu Leu Arg
        50                  55                  60

Lys Arg Tyr Glu Asp Leu Leu Thr Arg Leu Arg Ala Asn Gln Ser Trp
65                  70                  75                  80

Glu Asp Ser Asn Thr Asp Leu Val Pro Ala Pro Ala Val Arg Ile Leu
                85                  90                  95

Thr Pro Glu Val Arg Leu Gly Ser Gly Gly His Leu His Leu Arg Ile
            100                 105                 110

Ser Arg Ala Ala Leu Pro Glu Gly Leu Pro Glu Ala Ser Arg Leu His
        115                 120                 125

Arg Ala Leu Phe Arg Leu Ser Pro Thr Ala Ser Arg Ser Trp Asp Val
130                 135                 140

Thr Arg Pro Leu Arg Arg Gln Leu Ser Leu Ala Arg Pro Gln Ala Pro
145                 150                 155                 160

Ala Leu His Leu Arg Leu Ser Pro Pro Ser Gln Ser Asp Gln Leu
        165                 170                 175

Leu Ala Glu Ser Ser Ser Ala Arg Pro Gln Leu Glu Leu His Leu Arg
            180                 185                 190

Pro Gln Ala Ala Arg Gly Arg Arg Ala Arg Ala Arg Asn Gly Asp
        195                 200                 205

His Cys Pro Leu Gly Pro Gly Arg Cys Cys Arg Leu His Thr Val Arg
    210                 215                 220

Ala Ser Leu Glu Asp Leu Gly Trp Ala Asp Trp Val Leu Ser Pro Arg
```

```
                225                 230                 235                 240
Glu Val Gln Val Thr Met Cys Ile Gly Ala Cys Pro Ser Gln Phe Arg
                    245                 250                 255

Ala Ala Asn Met His Ala Gln Ile Lys Thr Ser Leu His Arg Leu Lys
                260                 265                 270

Pro Asp Thr Val Pro Ala Pro Cys Cys Val Pro Ala Ser Tyr Asn Pro
            275                 280                 285

Met Val Leu Ile Gln Lys Thr Asp Thr Gly Val Ser Leu Gln Thr Tyr
        290                 295                 300

Asp Asp Leu Leu Ala Lys Asp Cys His Cys Ile Gly Ser Gly Ser Gly
305                 310                 315                 320

Ser Gly

<210> SEQ ID NO 11
<211> LENGTH: 10
<212> TYPE: PRT
<213> ORGANISM: Artificial Sequence
<220> FEATURE:
<223> OTHER INFORMATION: Flag peptide

<400> SEQUENCE: 11

Asp Tyr Lys Asp Asp Asp Asp Lys Gly Gly
1               5                   10

<210> SEQ ID NO 12
<211> LENGTH: 10
<212> TYPE: PRT
<213> ORGANISM: Artificial Sequence
<220> FEATURE:
<223> OTHER INFORMATION: HA peptide

<400> SEQUENCE: 12

Tyr Pro Tyr Asp Val Pro Asp Tyr Ala Gly
1               5                   10

<210> SEQ ID NO 13
<211> LENGTH: 13
<212> TYPE: PRT
<213> ORGANISM: Artificial Sequence
<220> FEATURE:
<223> OTHER INFORMATION: peptide derived from human GDF-15

<400> SEQUENCE: 13

Glu Leu His Leu Arg Pro Gln Ala Ala Arg Gly Arg Arg
1               5                   10

<210> SEQ ID NO 14
<211> LENGTH: 13
<212> TYPE: PRT
<213> ORGANISM: Artificial Sequence
<220> FEATURE:
<223> OTHER INFORMATION: peptide derived from human GDF-15

<400> SEQUENCE: 14

Leu His Leu Arg Pro Gln Ala Ala Arg Gly Arg Arg Arg
1               5                   10

<210> SEQ ID NO 15
<211> LENGTH: 13
<212> TYPE: PRT
<213> ORGANISM: Artificial Sequence
<220> FEATURE:
<223> OTHER INFORMATION: peptide derived from human GDF-15
```

<400> SEQUENCE: 15

His Leu Arg Pro Gln Ala Ala Arg Gly Arg Arg Arg Ala
1               5                   10

<210> SEQ ID NO 16
<211> LENGTH: 13
<212> TYPE: PRT
<213> ORGANISM: Artificial Sequence
<220> FEATURE:
<223> OTHER INFORMATION: peptide derived from human GDF-15

<400> SEQUENCE: 16

Leu Arg Pro Gln Ala Ala Arg Gly Arg Arg Arg Ala Arg
1               5                   10

<210> SEQ ID NO 17
<211> LENGTH: 13
<212> TYPE: PRT
<213> ORGANISM: Artificial Sequence
<220> FEATURE:
<223> OTHER INFORMATION: peptide derived from human GDF-15

<400> SEQUENCE: 17

Arg Pro Gln Ala Ala Arg Gly Arg Arg Arg Ala Arg Ala
1               5                   10

<210> SEQ ID NO 18
<211> LENGTH: 13
<212> TYPE: PRT
<213> ORGANISM: Artificial Sequence
<220> FEATURE:
<223> OTHER INFORMATION: peptide derived from human GDF-15

<400> SEQUENCE: 18

Pro Gln Ala Ala Arg Gly Arg Arg Arg Ala Arg Ala Arg
1               5                   10

<210> SEQ ID NO 19
<211> LENGTH: 13
<212> TYPE: PRT
<213> ORGANISM: Artificial Sequence
<220> FEATURE:
<223> OTHER INFORMATION: peptide derived from human GDF-15

<400> SEQUENCE: 19

Gln Ala Ala Arg Gly Arg Arg Arg Ala Arg Ala Arg Asn
1               5                   10

<210> SEQ ID NO 20
<211> LENGTH: 13
<212> TYPE: PRT
<213> ORGANISM: Artificial Sequence
<220> FEATURE:
<223> OTHER INFORMATION: peptide derived from human GDF-15

<400> SEQUENCE: 20

Met His Ala Gln Ile Lys Thr Ser Leu His Arg Leu Lys
1               5                   10

<210> SEQ ID NO 21
<211> LENGTH: 291
<212> TYPE: DNA
<213> ORGANISM: Mus musculus

<400> SEQUENCE: 21
caagtgaagc tgcagcagtc aggccctggg atattgcagt cctcccagac cctcagtctg    60

```
acttgttctt tctctgggtt ttcactgagt acttctggta tgggtgtgag ctggattcgt    120
cagccttcag gaaagggtct ggagtggctg gcacacattt actgggatga tgacaagcgc    180
tataacccaa ccctgaagag ccggctcaca atctccaagg atccctccag aaaccaggta    240
ttcctcaaga tcaccagtgt ggacactgca gatactgcca catactactg t             291

<210> SEQ ID NO 22
<211> LENGTH: 264
<212> TYPE: DNA
<213> ORGANISM: Mus musculus

<400> SEQUENCE: 22
gacattgtgc tcacccagtc tccaaaattc atgtccacat cagtaggaga cagggtcagc    60
gtcacctgca aggccagtca gaatgtgggt actaatgtgg cctggtttct acagaaacca    120
gggcaatctc ctaaagcact tatttactcg gcatcctacc ggtacagtgg agtccctgat    180
cgcttcacag gcagtggatc tgggacagat ttcactctca ccatcagcaa cgtgcagtct    240
gaagacttgg cagagtattt ctgt                                           264

<210> SEQ ID NO 23
<211> LENGTH: 30
<212> TYPE: DNA
<213> ORGANISM: Mus musculus

<400> SEQUENCE: 23
gctcgaagtt cctacggggc aatggactac                                     30

<210> SEQ ID NO 24
<211> LENGTH: 27
<212> TYPE: DNA
<213> ORGANISM: Mus musculus

<400> SEQUENCE: 24
cagcaatata caactttcc gtacacg                                         27

<210> SEQ ID NO 25
<211> LENGTH: 16
<212> TYPE: PRT
<213> ORGANISM: Homo sapiens

<400> SEQUENCE: 25

Glu Val Gln Val Thr Met Cys Ile Gly Ala Cys Pro Ser Gln Phe Arg
1               5                   10                  15

<210> SEQ ID NO 26
<211> LENGTH: 21
<212> TYPE: PRT
<213> ORGANISM: Homo sapiens

<400> SEQUENCE: 26

Thr Asp Thr Gly Val Ser Leu Gln Thr Tyr Asp Leu Leu Ala Lys
1               5                   10                  15

Asp Cys His Cys Ile
                20
```

MONOCLONAL ANTIBODIES TO GROWTH AND DIFFERENTIATION FACTOR 15 (GDF-15)

CROSS-REFERENCE TO RELATED APPLICATIONS

This application is a continuation of U.S. patent application Ser. No. 14/431,281 (now abandoned), filed Mar. 25, 2015, which is a 35 U.S.C. § 371 filing of International Patent Application No. PCT/EP2013/070127, filed Sep. 26, 2013, which claims priority to European Patent Application No. 12186185.0, filed Sep. 26, 2012, each of which is incorporated by reference herein in its entirety.

FIELD OF THE INVENTION

The present invention relates to novel monoclonal anti-human-GDF-15 antibodies, pharmaceutical compositions, kits, methods and uses and the cell lines capable of producing the monoclonal antibodies described herein. The present invention further relates to novel antibodies to human GDF-15 capable of inhibiting cancer growth.

BACKGROUND

To date, many cancers are still areas of unmet medical needs, and accordingly, means to more effectively inhibit cancer growth, and to inhibit cancer growth in a broader range of cancers are needed.

Many types of cancer are known to express growth factors, including factors such as VEGF, PDGF, TGF-β and GDF-15.

GDF-15, growth and differentiation factor-15, is a divergent member of the TGF-β superfamily. It is a protein which is intracellularly expressed as a precursor, subsequently processed and eventually becomes secreted from the cell into the environment. Both the active, fully processed (mature) form and the precursor of GDF-15 can be found outside cells. The precursor covalently binds via its COOH-terminal amino acid sequence to the extracellular matrix (Bauskin A R et al., Cancer Research 2005) and thus resides on the exterior of a cell. The active, fully processed (mature) form of GDF-15 is soluble and is found in blood sera. Thus, the processed form of GDF-15 may potentially act on any target cell within the body that is connected to the blood circulation, provided that the potential target cell expresses a receptor for the soluble GDF-15 ligand.

During pregnancy, GDF-15 is found under physiological conditions in the placenta. However, many malignant cancers (especially aggressive brain cancers, melanoma, lung cancer, gastrointestinal tumors, colon cancer, pancreatic cancer, prostate cancer and breast cancer (Mimeault M and Batra S K, J. Cell Physiol 2010)) exhibit increased GDF-15 levels in the tumor as well as in blood serum. Likewise, correlations have been described between high GDF-15 expression and chemoresistance (Huang C Y et al., Clin. Cancer Res. 2009) and between high GDF-15 expression and poor prognosis, respectively (Brown D A et al., Clin. Cancer Res. 2009).

GDF-15 is expressed in gliomas of different WHO grades as assessed by immunohistochemistry (Roth et al., Clin. Cancer Res. 2010). Further, Roth et al. stably expressed short hairpin RNA-expressing DNA constructs targeting endogenous GDF-15 or control constructs in SMA560 glioma cells. When using these pre-established stable cell lines, they observed that tumor formation in mice bearing GDF-15 knockdown SMA560 cells was delayed compared to mice bearing control constructs.

Patent applications WO 2005/099746 and WO 2009/021293 relate to an anti-human-GDF-15 antibody (Mab26) capable of antagonizing effects of human GDF-15 on tumor-induced weight loss in vivo in mice: In these documents, immunologically compromised mice were administered with human tumor cells (prostate carcinoma cells DU145) transfected with plasmids overexpressing human GDF-15. Tumor cells carrying plasmids lacking a GDF-15 sequence served as a negative control. Those mice expressing xenograft GDF-15 exhibited a tumor-induced weight loss (clinical term: cachexia) and anorexia. A single intraperitoneal administration of 1 mg of Mab26 from WO 2005/099746 resulted in a complete reversal of tumor-induced weight loss. WO 2005/099746 and WO 2009/021293 do not disclose effects of an anti-human-GDF-15 antibody on tumor growth.

Similarly, Johnen H et al. (Nature Medicine, 2007) reported effects of an anti-human-GDF-15 monoclonal antibody on cancer-induced anorexia and weight loss but did not observe any effects of the anti-human-GDF-15 antibody on the size of the tumor formed by the cancer, even when the antibody was administered at a high dosage of 1 mg, and thus the antibody did not inhibit growth of the cancer.

Accordingly, to date, there was still a need in the art for means to effectively inhibit cancer growth, and for means to inhibit cancer growth in a broader range of cancers.

It is therefore an object of the invention to obtain means to effectively inhibit cancer growth, and means that can be used to inhibit cancer growth in a broader range of cancers.

In an effort to find novel means to inhibit cancer growth, the present inventors have surprisingly found that a novel monoclonal antibody to human GDF-15 can inhibit cancer growth of human xenograft tumors in mice.

Additionally, and in contrast to therapeutic antibodies known in the art, an antibody to human GDF-15 according to the present invention has an equilibrium dissociation constant of about 790 pM for recombinant GDF-15 even without additional affinity maturation, which is a higher affinity compared to most known therapeutic antibodies.

Thus, the antibody to human GDF-15 according to the present invention has superior properties compared to antibodies known from the art, and is particularly useful for inhibiting cancer growth. Accordingly, the present invention was completed.

BRIEF DESCRIPTION OF THE INVENTION

The present invention solves the above-mentioned objects by providing the monoclonal antibodies, pharmaceutical compositions, kits, uses and the cell lines capable of producing the monoclonal antibodies described herein.

In particular, the present inventors surprisingly show that novel monoclonal antibodies to human GDF-15 and antigen binding portions thereof according to the invention are capable of inhibiting cancer growth. This was unexpected because those monoclonal antibodies to GDF-15 that were previously known from the art (WO 2005/099746, WO 2009/021293 and Johnen H et al., Nature Medicine, 2007) were known to cause a reversal of cancer-induced weight loss (i.e. a reversal of a secondary symptom induced by the GDF-15 expressed by the cancer), but were shown to fail at inhibiting growth of the cancer.

By showing that the novel monoclonal antibodies to human GDF-according to the invention are capable of inhibiting cancer growth, the present inventors also surprisingly show that human GDF-15 protein can be targeted by the antibodies of the invention in a way that cancer growth is inhibited. It is expected that the same mechanism of cancer growth inhibition is applicable to a large number of cancers that overexpress human GDF-15 including the cancers listed below.

Thus, the present invention relates to a monoclonal antibody capable of binding to human GDF-15, or an antigen-binding portion thereof, wherein the heavy chain variable domain comprises a CDR3 region comprising the amino acid sequence of SEQ ID NO: 5 or an amino acid sequence at least 90% identical thereto, and wherein the light chain variable domain comprises a CDR3 region comprising the amino acid sequence of SEQ ID NO: 7 or an amino acid sequence at least 85% identical thereto.

The invention also relates to a pharmaceutical composition comprising the antibody or antigen-binding portion thereof according to the invention.

Further, the invention relates to an antibody or antigen-binding portion thereof or a pharmaceutical composition according to the invention for use in a method for treating cancer in a mammal, the method comprising administering the antibody or antigen-binding portion thereof or the pharmaceutical composition to said mammal.

Additionally, the invention relates to a kit comprising the pharmaceutical composition according to the invention.

The invention also relates to an expression vector comprising a nucleotide sequence encoding the antibody or antigen-binding portion thereof according to the invention.

Further, the invention relates to a cell line capable of producing an antibody or antigen-binding portion thereof according to the invention.

Thus, by providing novel monoclonal antibodies to human GDF-15, the present invention provides a novel cancer growth inhibitor that meets the above-defined needs in the art.

Figure 1:
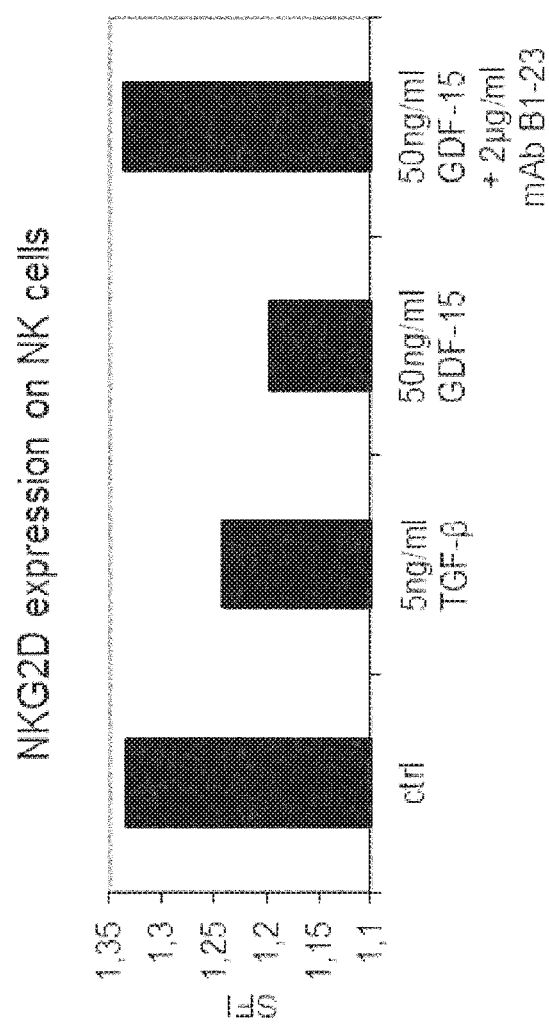
FIG. 1: NKG2D Expression on NK Cells after Treatment with or without GDF-15. The cell surface expression of NKG2D was determined on NK cells after treatment with the indicated cytokines in the presence or absence of the anti-GDF-15 antibody mAb B1-23. The figure displays specific fluorescence intensities determined by flow cytometry, quantified relative to an unspecific control antibody.

An anti-tumor effect of B1-23 in vivo. Balb/c$^{nu/nu}$ nude mice were used in a xenograft setting with the melanoma cell line UACC-257. The tumor size of the animal cohort treated with B1-23 (open squares) was significantly decreased, compared to the PBS control group (filled solid circles). Significance was defined as p<0.05 as assessed by Wilcoxon's log-rank test.

DETAILED DESCRIPTION OF THE INVENTION

Definitions

Unless otherwise defined below, the terms used in the present invention shall be understood in accordance with their common meaning known to the person skilled in the art.

The term "antibody" as used herein refers to any functional antibody that is capable of specific binding to the antigen of interest, as generally outlined in chapter 7 of Paul, W. E. (Ed.): Fundamental Immunology 2nd Ed. Raven Press, Ltd., New York 1989, which is incorporated herein by reference. Without particular limitation, the term "antibody" encompasses antibodies from any appropriate source species, including chicken and mammalian such as mouse, goat, non-human primate and human. Preferably, the antibody is a humanized antibody. The antibody is preferably a monoclonal antibody which can be prepared by methods well-known in the art. The term "antibody" encompasses an IgG-1, -2, -3, or -4, IgE, IgA, IgM, or IgD isotype antibody. The term "antibody" encompasses monomeric antibodies (such as IgD, IgE, IgG) or oligomeric antibodies (such as IgA or IgM). The term "antibody" also encompasses—without particular limitations—isolated antibodies and modified antibodies such as genetically engineered antibodies, e.g. chimeric antibodies.

The nomenclature of the domains of antibodies follows the terms as known in the art. Each monomer of an antibody comprises two heavy chains and two light chains, as generally known in the art. Of these, each heavy and light chain comprises a variable domain (termed $V_H$ for the heavy chain and $V_L$ for the light chain) which is important for antigen binding. These heavy and light chain variable domains comprise (in an N-terminal to C-terminal order) the regions FR1, CDR1, FR2, CDR2, FR3, CDR3, and FR4 (FR, framework region; CDR, complementarity determining region which is also known as hypervariable region). The identification and assignment of the above-mentioned antibody regions within the antibody sequence is generally in accordance with Kabat et al. (Sequences of proteins of immunological interest, U.S. Dept. of Health and Human Services, Public Health Service, National Institutes of Health, Bethesda, Md. 1983), or Chothia et al. (Conformations of immunoglobulin hypervariable regions. Nature. 1989 Dec. 21-28; 342(6252):877-83), or may be performed by using the IMGT/V-QUEST software described in Giudicelli et al. (IMGT/V-QUEST, an integrated software program for immunoglobulin and T cell receptor V-J and V-D-J rearrangement analysis. Nucleic Acids Res. 2004 Jul. 1; 32 (Web Server issue):W435-40), which is incorporated herein by reference. Preferably, the antibody regions indicated above are identified and assigned by using the IMGT/V-QUEST software.

A "monoclonal antibody" is an antibody from an essentially homogenous population of antibodies, wherein the antibodies are substantially identical in sequence (i.e. identical except for minor fraction of antibodies containing naturally occurring sequence modifications such as amino acid modifications at their N- and C-termini). Unlike polyclonal antibodies which contain a mixture of different antibodies directed to numerous epitopes, monoclonal antibodies are directed to the same epitope and are therefore highly specific. The term "monoclonal antibody" includes (but is not limited to) antibodies which are obtained from a monoclonal cell population derived from a single cell clone, as for instance the antibodies generated by the hybridoma method described in Köhler and Milstein (Nature, 1975 Aug. 7; 256(5517):495-7) or Harlow and Lane ("Antibodies: A Laboratory Manual" Cold Spring Harbor Laboratory Press, Cold Spring Harbor, N.Y. 1988). A monoclonal antibody may also be obtained from other suitable methods, including phage display techniques such as those described in Clackson et al. (Nature. 1991 Aug. 15; 352(6336):624-8) or Marks et al. (J Mol Biol. 1991 Dec. 5; 222(3):581-97). A monoclonal antibody may be an antibody that has been optimized for antigen-binding properties such as decreased Kd values, optimized association and dissociation kinetics by methods known in the art. For instance, Kd values may be optimized by display methods including phage display, resulting in affinity-matured monoclonal antibodies. The term "monoclonal antibody" is not limited to antibody sequences from particular species of origin or from one single species of origin. Thus, the meaning of the term "monoclonal antibody" encompasses chimeric monoclonal antibodies such as humanized monoclonal antibodies.

"Humanized antibodies" are antibodies which contain human sequences and a minor portion of non-human sequences which confer binding specificity to an antigen of interest (e.g. human GDF-15). Typically, humanized antibodies are generated by replacing hypervariable region sequences from a human acceptor antibody by hypervariable region sequences from a non-human donor antibody (e.g. a mouse, rabbit, rat donor antibody) that binds to an antigen of interest (e.g. human GDF-15). In some cases, framework region sequences of the acceptor antibody may also be replaced by the corresponding sequences of the donor antibody. In addition to the sequences derived from the donor and acceptor antibodies, a "humanized antibody" may either contain other (additional or substitute) residues or sequences or not. Such other residues or sequences may serve to further improve antibody properties such as binding properties (e.g. to decrease Kd values) and/or immunogenic properties (e.g. to decrease antigenicity in humans). Non-limiting examples for methods to generate humanized antibodies are known in the art, e.g. from Riechmann et al. (Nature. 1988 Mar. 24; 332(6162):323-7) or Jones et al. (Nature. 1986 May 29-Jun. 4; 321(6069):522-5).

The term "human antibody" relates to an antibody containing human variable and constant domain sequences. This definition encompasses antibodies having human sequences bearing single amino acid substitutions or modifications which may serve to further improve antibody properties such as binding properties (e.g. to decrease Kd values) and/or immunogenic properties (e.g. to decrease antigenicity in humans). The term "human antibody" excludes humanized antibodies where a portion of non-human sequences confers binding specificity to an antigen of interest.

An "antigen-binding portion" of an antibody as used herein refers to a portion of an antibody that retains the capability of the antibody to specifically bind to the antigen (e.g. GDF-15), i.e. the "antigen-binding portion" is capable of competing with the antibody for specific binding to the antigen. The "antigen-binding portion" may contain one or more fragments of the antibody. Without particular limitation, it can be produced by any suitable method known in the art, including recombinant DNA methods and preparation by chemical or enzymatic fragmentation of antibodies. Antigen-binding portions may be Fab fragments, F(ab') fragments, F(ab')$_2$ fragments, single chain antibodies (scFv), single-domain antibodies, diabodies or any other portion(s) of the antibody that allow(s) to retain binding to the antigen.

An "antibody" (e.g. a monoclonal antibody) or an "antigen-binding portion" may have been derivatized or be linked to a different molecule. For example, molecules that may be linked to the antibody are other proteins (e.g. other antibodies), a molecular label (e.g. a fluorescent, luminescent, colored or radioactive molecule), a pharmaceutical and/or a toxic agent. The antibody or antigen-binding portion may be linked directly (e.g. in form of a fusion between two proteins), or via a linker molecule (e.g. any suitable type of chemical linker known in the art).

As used herein, the terms "binding" or "bind" refer to specific binding to the antigen of interest (e.g. human GDF-15). Preferably, the Kd value is less than 100 nM, more preferably less than 50 nM, still more preferably less than nM, still more preferably less than 5 nM and most preferably less than 2 nM.

The term "epitope" as used herein refers to a small portion of an antigen that forms the binding site for an antibody.

In the context of the present invention, binding or competitive binding of antibodies or their antigen-binding portions to the antigen of interest (e.g. human GDF-15) is measured by using surface plasmon resonance measurements as a reference standard assay, as described below.

The terms "$K_D$" or "$K_D$ value" relate to the equilibrium dissociation constant as known in the art. In the context of the present invention, these terms relate to the equilibrium dissociation constant of an antibody with respect to a particular antigen of interest (e.g. human GDF-15) The equilibrium dissociation constant is a measure of the propensity of a complex (e.g. an antigen-antibody complex) to reversibly dissociate into its components (e.g. the antigen and the antibody). For the antibodies according to the invention, $K_D$ values (such as those for the antigen human GDF-15) are generally determined by using surface plasmon resonance measurements as described below.

The term "cancer growth" as used herein relates to any measurable growth of the cancer. For cancers forming solid tumors, "cancer growth" relates to a measurable increase in tumor volume over time. If the cancer has formed only a single tumor, "cancer growth" relates only to the increase in volume of the single tumor. If the cancer has formed multiple tumors such as metastases, "cancer growth" relates to the increase in volume of all measurable tumors. For solid tumors, the tumor volume can be measured by any method known in the art, including magnetic resonance imaging and computed tomography (CT scan).

For leukemias which are characterized by the presence of cancerous cells of the blood system in blood, "cancer growth" relates to a measurable increase in the number of cancer cells per blood volume. In order to carry out such measurements, cancer cells can be identified from blood samples by using any method known in the art, including cell morphology measurements, or staining of tumor cell marker proteins such as tumor marker cell surface proteins, e.g. by staining with specific antibodies, and the cancer cells can be counted.

Terms such as "inhibiting cancer growth" as used herein refer to a measurable inhibition of cancer growth in patient treated with the antibody. Preferably, the inhibition is statistically significant. Inhibition of cancer growth may be assessed by comparing cancer growth in a group of patients treated in accordance with the present invention to a control group of untreated patients, or by comparing a group of patients that receive a standard cancer treatment of the art plus a treatment according to the invention with a control group of patients that only receive a standard cancer treatment of the art. Such studies for assessing the inhibition of cancer growth are designed in accordance with accepted standards for clinical studies, e.g. double-blinded, randomized studies with sufficient statistical power. The term "inhibiting cancer growth" includes an inhibition of cancer growth where the cancer growth is inhibited partially (i.e. where the cancer growth in the patient is delayed compared to the control group of patients), an inhibition where the cancer growth is inhibited completely (i.e. where the cancer growth in the patient is stopped), and an inhibition where cancer growth is reversed (i.e. the cancer shrinks).

An "isolated antibody" as used herein is an antibody that has been identified and separated from the majority of components (by weight) of its source environment, e.g. from the components of a hybridoma cell culture or a different cell culture that was used for its production (e.g. producer cells such as CHO cells that recombinantly express the antibody). The separation is performed such that it sufficiently removes components that may otherwise interfere with the suitability of the antibody for the desired applications (e.g. with a therapeutic use of the anti-human GDF-15 antibody according to the invention). Methods for preparing isolated antibodies are known in the art and include Protein A chromatography, anion exchange chromatography, cation exchange chromatography, virus retentive filtration and ultrafiltration. Preferably, the isolated antibody preparation is at least 70% pure (w/w), more preferably at least 80% pure (w/w), still more preferably at least 90% pure (w/w), still more preferably at least 95% pure (w/w), and most preferably at least 99% pure (w/w), as measured by using the Lowry protein assay.

A "diabody" as used herein is a small bivalent antigen-binding antibody portion which comprises a heavy chain variable domain linked to a light chain variable domain on the same polypeptide chain linked by a peptide linker that is too short to allow pairing between the two domains on the same chain. This results in pairing with the complementary domains of another chain and in the assembly of a dimeric molecule with two antigen binding sites. Diabodies may be bivalent and monospecific (such as diabodies with two antigen binding sites for human GDF-15), or may be bivalent and bispecific (e.g. diabodies with two antigen binding sites, one being a binding site for human GDF-15, and the other one being a binding site for a different antigen). A detailed description of diabodies can be found in Holliger P et al. (""Diabodies": small bivalent and bispecific antibody fragments." Proc Natl Acad Sci USA. 1993 Jul. 15; 90(14): 6444-8).

A "single-domain antibody" (which is also referred to as "Nanobody™") as used herein is an antibody fragment consisting of a single monomeric variable antibody domain. Structures of and methods for producing single-domain antibodies are known from the art, e.g. from Holt L J et al. ("Domain antibodies: proteins for therapy." Trends Biotechnol. 2003 November; 21(11):484-90), Saerens D et al. ("Single-domain antibodies as building blocks for novel therapeutics." Curr Opin Pharmacol. 2008 October; 8(5): 600-8. Epub 2008 Aug. 22), and Arbabi Ghahroudi M et al. ("Selection and identification of single domain antibody fragments from camel heavy-chain antibodies." FEBS Lett. 1997 Sep. 15; 414(3):521-6).

The term "higher" as used herein means that a value (e.g. a GDF-15 level) in a patient sample is higher than a value in a corresponding control sample or group of control samples. Preferably, the difference is statistically significant.

The term "elevated GDF-15 levels" as used herein means that the human patient has higher GDF-15 levels in blood serum before administration of the antibody or antigen-binding portion thereof or the pharmaceutical composition according to the invention, when compared to median GDF-15 levels in blood sera of healthy human control individuals as a reference.

A preferred median reference for GDF-15 level in blood sera of healthy human control individuals is <0.8 ng/ml. The expected range is between 0.2 ng/ml and 1.2 ng/ml in healthy human controls (Reference: Tanno T et al.: "Growth differentiation factor 15 in erythroid health and disease." Curr Opin Hematol. 2010 May; 17(3): 184-190).

Preferably, the levels are 1.2-fold higher, more preferably 1.5-fold higher, still more preferably 2-fold higher and most preferably 5-fold higher.

The term "prior to administration" as used herein means the period of time immediately before administration of the antibody, fragment thereof or the pharmaceutical composition according to the invention. Preferably, the term "prior to administration" means a period of 30 days immediately before administration; most preferably a period of one week immediately before administration.

The terms "significant", "significantly", etc. as used herein refer to a statistically significant difference between values.

The terms "cancer" and "cancer cell" is used herein in accordance with their common meaning in the art (see for instance Weinberg R. et al.: The Biology of Cancer. Garland Science: New York 2006. 850p).

In accordance with the present invention, each occurrence of the term "comprising" may optionally be substituted with the term "consisting of".

Methods and Techniques

Generally, unless otherwise defined herein, the methods used in the present invention (e.g. cloning methods or methods relating to antibodies) are performed in accordance with procedures known in the art, e.g. the procedures described in Sambrook et al. ("Molecular Cloning: A Laboratory Manual.", $2^{nd}$ Ed., Cold Spring Harbor Laboratory Press, Cold Spring Harbor, N.Y. 1989), Ausubel et al. ("Current Protocols in Molecular Biology." Greene Publishing Associates and Wiley Interscience; New York 1992), and Harlow and Lane ("Antibodies: A Laboratory Manual" Cold Spring Harbor Laboratory Press, Cold Spring Harbor, N.Y. 1988), all of which are incorporated herein by reference.

Binding of monoclonal anti-human-GDF-15 antibodies according to the invention is generally assessed by employing surface plasmon resonance measurements using a Biorad ProteOn XPR36 system and Biorad G L C sensor chips as described for anti-human GDF-15 mAb-B1-23 in Example 1.

Sequence Alignments of sequences according to the invention are performed by using the BLAST algorithm (see Altschul et al. (1990) "Basic local alignment search tool." Journal of Molecular Biology 215. p. 403-410; Altschul et al.: (1997) Gapped BLAST and PSI-BLAST: a new generation of protein database search programs. Nucleic Acids Res. 25:3389-3402). Preferably, the following parameters are used: Max target sequences 10; Word size 3; BLOSUM 62 matrix; gap costs: existence 11, extension 1; conditional compositional score matrix adjustment. Thus, when used in connection with sequences, terms such as "identity" or "identical" refer to the identity value obtained by using the BLAST algorithm.

Monoclonal antibodies according to the invention can be produced by any method known in the art, including but not limited to the methods referred to in Siegel D L ("Recombinant monoclonal antibody technology." Transfus Clin Biol. 2002 January; 9(1):15-22). In a preferred embodiment, an antibody according to the invention is produced by the hybridoma cell line B1-23 deposited with the Deutsche Sammlung für Mikroorganismen and Zellkulturen GmbH (DSMZ) under the accession No. DSM ACC3142 under the Budapest treaty. The deposit was filed on Sep. 29, 2011.

Cell proliferation can be measured by suitable methods known in the art, including (but not limited to) visual microscopy, metabolic assays such as those which measure mitochondrial redox potential (e.g. MTT (3-(4,5-Dimethylthiazol-2-yl)-2,5-diphenyltetrazolium bromide) assay; Resazurin staining which is also known as Alamar Blue® assay), staining of known endogenous proliferation biomarkers (e.g. Ki-67), and methods measuring cellular DNA synthesis (e.g. BrdU and [$^3$H]-Thymidine incorporation assays).

Immunosuppression can be measured by suitable methods known in the art, including (but not limited to) immune cell proliferation, cytokine secretion, intracellular cytokine staining by flow cytometry, cytokine measurement by qRT-PCR, redirected target cell lysis, further cytotoxicity or degranulation assays, downregulation of activating immune cell receptors (like NKG2D), upregulation of inhibitory immune cell receptors, immunological synapse formation, immune cell infiltration. For the term immunosuppression to apply, an effect shall be measurable in at least one of these or in any other suitable assay. The lack of effect in a specific test does not imply a general absence of immunosuppression.

Human GDF-15 levels can be measured by any method known in the art, including measurements of GDF-15 mRNA levels by methods including (but not limited to) quantitative real-time PCR (qRT-PCR) for human GDF-15 mRNA using primers specific to human GDF-15, mRNA in situ hybridization with probes specific to human GDF-15, mRNA deep sequencing methods; and including measurements of GDF-15 protein levels by methods including (but not limited to) mass spectrometry for proteins or peptides derived from human GDF-15, Western Blotting using antibodies specific to human GDF-15, flow cytometry using antibodies specific to human GDF-15, strip tests using antibodies specific to human GDF-15, or immunocytochemistry using antibodies specific to human GDF-15. For such methods using antibodies specific to human GDF-15, the anti-human GDF-15 antibodies of the present invention are preferred, and the antibody of the invention produced by the hybridoma cell line B1-23 deposited with the Deutsche Sammlung für Mikroorganismen and Zellkulturen GmbH (DSMZ) under the accession No. DSM ACC3142 is most preferred.

EMBODIMENTS OF THE INVENTION

As described above, the inventors show that human GDF-15 protein can be targeted by an antibody of the invention in a way that cancer growth is inhibited.

This is a surprising finding in view of the art teaching that only cancer-induced weight loss can be reversed by anti-GDF-antibodies, and that growth of the cancer cannot be inhibited (WO 2005/099746, WO 2009/021293 and Johnen H et al., Nature Medicine, 2007).

When taking into account the present invention, it becomes clear that the anti-GDF-15 antibodies known from WO 2005/099746, WO 2009/021293 and Johnen H et al., Nature Medicine, 2007 only inhibit one of the effects of human GDF-15 (i.e. cancer-induced weight loss), but fail to inhibit other effects of human GDF-15 such as those related to cancer growth. In view of the present invention, one possible explanation for this failure is that the antibodies known from the above documents may only interfere with transport of human GDF-15 across the blood-brain barrier (by forming a large complex that cannot be transported across the blood-brain barrier) but are incapable of binding human GDF-15 in a way that renders it generally unable to interact with its receptor (e.g. a receptor residing on cells outside the brain).

The following properties of the antibodies of the present invention are expected to contribute to their capability of inhibiting the effects of human GDF-15 more completely, including the inhibition of cancer growth:

Broad Binding Specificity to Forms of Human GDF-15

The antibodies of the present invention are capable of binding to mature recombinant human GDF-15 (represented by SEQ ID No: 8) and are therefore capable of binding to active, fully processed (mature) human GDF-15.

Additionally, by performing staining experiments with the mAb-B1-23 antibody according to the invention on human cells, the inventors show that the mAb-B1-23 antibody according to the invention is capable of binding to the human GDF-15 precursor on human cells.

Thus, it is expected that binding and effects of the antibodies of the present invention (e.g. the inhibition of cancer growth) are not limited to effects on a particular form of human GDF-15.

High Binding Affinity

The antibodies and antigen binding portions thereof according to the invention have high binding affinity, as demonstrated by the mAb-B1-23 antibody according to the invention which has an equilibrium dissociation constant of about 790 pM for recombinant human GDF-15. Notably, such affinity values are superior to most of the existing therapeutic antibodies, e.g. to the therapeutic antibody Rituximab which has an equilibrium dissociation constant of about 8 nM.

High binding affinity will ensure that the antibody to human GDF-15 according to the invention stably binds to human GDF-15, such that effects of human GDF-15 including effects on cancer growth are effectively inhibited.

Binding to a Discontinuous or Conformational Epitope

The antibodies and antigen binding portions thereof according to the invention bind to a discontinuous or conformational epitope, as demonstrated below for the mAb-B1-23 antibody according to the invention.

Binding of antibodies and antigen binding portions thereof according to the invention to a discontinuous or conformational GDF-15 epitope may help to keep human GDF-15 in a specific conformation and thereby contribute to the effective inhibition of effects of human GDF-15 including effects on cancer growth.

Thus, the invention relates to the following embodiments:

A) ANTIBODIES, VECTORS AND CELL LINES

Concretely, the invention relates to a monoclonal antibody capable of binding to human GDF-15, or an antigen-binding portion thereof, wherein the heavy chain variable domain comprises a CDR3 region comprising the amino acid sequence of SEQ ID NO: 5 or an amino acid sequence at least 90% identical thereto, and wherein the light chain variable domain comprises a CDR3 region comprising the amino acid sequence of SEQ ID NO: 7 or an amino acid sequence at least 85% identical thereto.

Alternatively, the invention relates to a monoclonal antibody capable of binding to human GDF-15, or an antigen-binding portion thereof, wherein the heavy chain variable domain comprises a CDR3 region comprising the amino acid sequence of SEQ ID NO: 5 or an amino acid sequence that differs by not more than one amino acid from the amino acid sequence of SEQ ID NO: 5, and wherein the light chain variable domain comprises a CDR3 region comprising the amino acid sequence of SEQ ID NO: 7 or an amino acid sequence or an amino acid sequence that differs by not more than one amino acid from the amino acid sequence of SEQ ID NO: 7.

In a second embodiment in accordance with the above embodiments, the heavy chain variable domain of the monoclonal antibody or antigen-binding portion thereof comprises a CDR3 region comprising the amino acid sequence of SEQ ID NO: 5, or the light chain variable domain comprises a CDR3 region comprising the amino acid sequence of SEQ ID NO: 7.

In a third embodiment in accordance with the above embodiments, the heavy chain variable domain of the monoclonal antibody or antigen-binding portion thereof comprises a CDR3 region comprising the amino acid sequence of SEQ ID NO: 5, and the light chain variable domain comprises a CDR3 region comprising the amino acid sequence of SEQ ID NO: 7.

In still another embodiment in accordance with the above embodiments, the heavy chain variable domain comprises a region comprising an FR1, a CDR1, an FR2, a CDR2 and an FR3 region and comprising the amino acid sequence of SEQ ID NO: 1 or a sequence 85%, 90%, 91%, 92%, 93%, 94%, 95%, 96%, 97%, 98% or 99% identical thereto, and the light chain variable domain comprises a region comprising an FR1, a CDR1, an FR2, a CDR2 and an FR3 region and comprising the amino acid sequence of SEQ ID NO: 2 or a sequence 85%, 90%, 91%, 92%, 93%, 94%, 95%, 96%, 97%, 98% or 99% identical thereto.

In a preferred embodiment in accordance with the above embodiments, the heavy chain variable domain comprises a region comprising an FR1, a CDR1, an FR2, a CDR2 and an FR3 region and comprising the amino acid sequence of SEQ ID NO: 1 or a sequence 95% identical thereto, and the light chain variable domain comprises a region comprising an FR1, a CDR1, an FR2, a CDR2 and an FR3 region and comprising the amino acid sequence of SEQ ID NO: 2 or a sequence 95% identical thereto.

In a more preferred embodiment in accordance with the above embodiments, the heavy chain variable domain comprises a region comprising an FR1, a CDR1, an FR2, a CDR2 and an FR3 region and comprising the amino acid sequence of SEQ ID NO: 1 or a sequence 98% identical thereto, and the light chain variable domain comprises a region comprising an FR1, a CDR1, an FR2, a CDR2 and an FR3 region and comprising the amino acid sequence of SEQ ID NO: 2 or a sequence 98% identical thereto.

In a still more preferred embodiment in accordance with the above embodiments, the heavy chain variable domain comprises a region comprising an FR1, a CDR1, an FR2, a CDR2 and an FR3 region and comprising the amino acid sequence of SEQ ID NO: 1, and the light chain variable domain comprises a region comprising an FR1, a CDR1, an FR2, a CDR2 and an FR3 region and comprising the amino acid sequence of SEQ ID NO: 2.

The invention also relates to a monoclonal antibody capable of binding to human GDF-15, or an antigen-binding portion thereof, wherein the heavy chain variable domain comprises a CDR1 region comprising the amino acid sequence of SEQ ID NO: 3 and a CDR2 region comprising the amino acid sequence of SEQ ID NO: 4, and wherein the light chain variable domain comprises a CDR1 region comprising the amino acid sequence of SEQ ID NO: 6 and a CDR2 region comprising the amino acid sequence of SEQ ID NO: 7. In a preferred aspect of this embodiment, the antibody may have CDR3 sequences as defined in any of the embodiments of the invention described above.

In another embodiment, the invention relates to a monoclonal antibody capable of binding to human GDF-15, or an antigen-binding portion thereof, wherein the antibody or antigen-binding portion thereof is capable of inhibiting cancer growth in a mammal, preferably a human patient.

In another embodiment in accordance with the above embodiment, the invention relates to an antigen-binding portion capable of binding to human GDF-15, wherein the antigen-binding portion is a single-domain antibody (also referred to as "Nanobody™"). In one aspect of this embodiment, the single-domain antibody comprises the CDR1, CDR2, and CDR3 amino acid sequences of SEQ ID NO: 3, SEQ ID NO: 4, and SEQ ID NO: 5, respectively. In another aspect of this embodiment, the single-domain antibody comprises the CDR1, CDR2, and CDR3 amino acid sequences of SEQ ID NO: 6, SEQ ID NO: 7, and SEQ ID NO: 7, respectively. In a preferred aspect of this embodiment, the single-domain antibody is a humanized antibody.

Preferably, the antibodies of the invention capable of binding to human GDF-15 or the antigen-binding portions thereof have an equilibrium dissociation constant for human GDF-15 that is equal to or less than 100 nM, less than 20 nM, preferably less than 10 nM, more preferably less than 5 nM and most preferably between 0.1 nM and 2 nM.

In another embodiment of the invention, the antibody capable of binding to human GDF-15 or the antigen-binding portion thereof binds to the same human GDF-15 epitope as the antibody to human GDF-15 obtainable from the cell line B1-23 deposited with the Deutsche Sammlung für Mikroorganismen and Zellkulturen GmbH (DMSZ) under the accession No. DSM ACC3142. As described herein, antibody binding to human GDF-15 in accordance with the present invention is assessed by surface plasmon resonance measurements as a reference standard method, in accordance with the procedures described in Example 1. Binding to the same epitope on human GDF-15 can be assessed similarly by surface plasmon resonance competitive binding experiments of the antibody to human GDF-15 obtainable from the cell line B1-23 and the antibody that is expected to bind to the same human GDF-15 epitope as the antibody to human GDF-15 obtainable from the cell line B1-23.

In a very preferred embodiment, the antibody of the invention is the monoclonal antibody capable of binding to human GDF-15 obtainable from the cell line B1-23 deposited with the Deutsche Sammlung für Mikroorganismen und Zellkulturen GmbH (DMSZ) under the accession No. DSM ACC3142 or an antigen-binding portion thereof.

In a preferred embodiment, the antibody capable of binding to human GDF-15 or the antigen-binding portion thereof according to the invention is a humanized monoclonal antibody or an antigen-binding portion thereof. For any given non-human antibody sequence in accordance with the invention (i.e. a donor antibody sequence), humanized monoclonal anti-human-GDF-15 antibodies of the invention or antigen-binding portions thereof can be generated in accordance with techniques known in the art, as described above.

In a very preferred embodiment, the monoclonal antibody capable of binding to human GDF-15 or antigen-binding portion thereof is a humanized antibody derived from the monoclonal antibody capable of binding to human GDF-15 obtainable from the cell line B1-23 deposited with the Deutsche Sammlung für Mikroorganismen und Zellkulturen GmbH (DMSZ) under the accession No. DSM ACC3142, or an antigen-binding portion thereof. In a non-limiting aspect of this embodiment, the heavy chain variable domain of the humanized antibody or antigen-binding portion thereof comprises a CDR3 region comprising the amino acid sequence of SEQ ID NO: 5, and the light chain variable domain of the humanized antibody or antigen-binding portion thereof comprises a CDR3 region comprising the amino acid sequence of SEQ ID NO: 7. In a further non-limiting aspect of this embodiment, the heavy chain variable domain of the humanized antibody or antigen-binding portion thereof comprises or further comprises a CDR1 region comprising the amino acid sequence of SEQ ID NO: 3 and a CDR2 region comprising the amino acid sequence of SEQ ID NO: 4, and the light chain variable domain of the humanized antibody or antigen-binding portion thereof comprises or further comprises a CDR1 region comprising the amino acid sequence of SEQ ID NO: 6 and a CDR2 region comprising the amino acid sequence of SEQ ID NO: 7.

The present invention also relates to a monoclonal antibody capable of binding to human GDF-15, or an antigen-binding portion thereof, wherein the binding is binding to a conformational or discontinuous epitope on human GDF-15 comprised by the amino acid sequences of SEQ ID No: 25 and SEQ ID No: 26. In a preferred aspect of this embodiment, the antibody or antigen-binding portion thereof is an antibody or antigen-binding portion thereof as defined in any one of the above embodiments.

In another embodiment of the invention in accordance with the above embodiments, the antibody capable of binding to human GDF-15 or the antigen-binding portion thereof is a diabody. In one aspect of this embodiment, the diabody is bivalent and monospecific, with two identical antigen binding sites for human GDF-15. In a second, alternative aspect of this embodiment, the diabody is bivalent and bispecific, with one antigen binding site being a binding site for human GDF-15, and the other antigen binding site being a binding site for a different antigen. Non-limiting examples for the different antigen according to this second aspect of this embodiment are i) cell surface antigens that are co-expressed with GDF-15 at high levels on the same cancer (e.g. at higher levels compared to a control sample of the same patient obtained from a non-cancerous part of the tissue which is the tissue of origin of the cancer), and ii) cell surface antigens on cells of the immune system which are known as useful antigens for the recruitment of cells of the immune system to the tumor.

In still another embodiment of the invention in accordance with the above embodiments, the antibody capable of binding to human GDF-15 or the antigen-binding portion thereof is linked to a drug. In non-limiting aspects of this embodiment, the drug can be a known anticancer agent and/or an immune-stimulatory molecule. Known anticancer agents include alkylating agents such as cisplatin, carboplatin, oxaliplatin, mechlorethamine, cyclophosphamide, chlorambucil, and ifosfamide; anti-metabolites such as azathioprine and mercaptopurine; alkaloids such as vinca alkaloids (e.g. vincristine, vinblastine, vinorelbine, and vindesine), taxanes (e.g. paclitaxel, docetaxel) etoposide and teniposide; topoisomerase inhibitors such as camptothecins (e.g. irinotecan and topotecan); cytotoxic antibiotics such as actinomycin, anthracyclines, doxorubicin, daunorubicin, valrubicin, idarubicin, epirubicin, bleomycin, plicamycin and mitomycin; and radioisotopes. Linking of the antibodies or the antigen-binding portions thereof of the invention to anticancer agents is expected to result in stronger cancer tumor growth inhibition compared to the antibody without the anticancer agent, because the resulting conjugate will accumulate at the site of the tumor due to the presence of GDF-15 in the tumor, leading to the accumulation of the anticancer agent at the site of the tumor and to enhanced effects of the anticancer agent on the tumor.

In a further embodiment in accordance with the above embodiments, the antibody capable of binding to human GDF-15 or the antigen-binding portion thereof is modified by an amino acid tag. Non-limiting examples of such tags include Polyhistidin (His–) tags, FLAG-tag, Hemagglutinin (HA) tag, glycoprotein D (gD) tag, and c-myc tag. Tags may be used for various purposes. For instance, they may be used to assist purification of the antibody capable of binding to human GDF-15 or the antigen-binding portion thereof, or they may be used for detection of the antibody or the antigen-binding portion thereof (e.g. when used in diagnostic assays). Preferably, such tags are present at the C-terminus or N-terminus of the antibody capable of binding to human GDF-15 or the antigen-binding portion thereof.

In a preferred embodiment of the present invention in accordance with the above embodiments, the antibody capable of binding to human GDF-15 or the antigen-binding portion thereof is capable of inhibiting cancer growth in a mammal, preferably a human patient.

In another preferred embodiment of the present invention in accordance with the above embodiments, the human GDF-15 is recombinant human GDF-15 having the amino acid sequence represented by SEQ ID No: 8.

In still another preferred embodiment of the present invention in accordance with the above embodiments, the binding of the antibody capable of binding to human GDF-15 or the antigen-binding portion thereof is a binding to a conformational or discontinuous epitope on human GDF-15.

Preferably, the monoclonal antibodies of the present invention capable of binding to human GDF-15 or the antigen-binding portions thereof are isolated antibodies.

The invention also relates to an expression vector comprising a nucleotide sequence encoding the antibody or antigen-binding portion thereof as defined above.

Further, the present invention also provides a cell line capable of producing an antibody or antigen-binding portion thereof according to the present invention.

In one embodiment, the cell line can be derived from any cell line that is known in that art and suitable for the production of antibodies or antigen-binding portions thereof.

In a preferred embodiment, the cell line is the cell line 31-23 deposited with the Deutsche Sammlung far Mikroorganismen and Zellkulturen GmbH (DMSZ) under the accession No. DSM ACC3142.

In another preferred embodiment, the cell line contains an expression vector according to the invention as defined above.

B) PHARMACEUTICAL COMPOSITIONS

In a further embodiment, the present invention relates to a pharmaceutical composition comprising any of the antibodies or antigen-binding portions thereof as defined above.

Pharmaceutical compositions in accordance with the present invention are prepared in accordance with known standards for the preparation of pharmaceutical compositions containing antibodies and portions thereof.

For instance, the compositions are prepared in a way that they can be stored and administered appropriately, e.g. by using pharmaceutically acceptable components such as carriers, excipients or stabilizers.

Such pharmaceutically acceptable components are not toxic in the amounts used when administering the pharmaceutical composition to a patient. The pharmaceutical acceptable components added to the pharmaceutical compositions may depend on the particular intended use of the pharmaceutical compositions and the route of administration.

In general, the pharmaceutically acceptable components used in connection with the present invention are used in accordance with knowledge available in the art, e.g. from Remington's Pharmaceutical Sciences, Ed. AR Gennaro, 20th edition, 2000, Williams & Wilkins, PA, USA.

C) THERAPEUTIC METHODS AND PRODUCTS FOR USE IN THESE METHODS

The present invention further relates to a method for treating a cancer in a mammal, the method comprising administering an antibody or antigen-binding portion thereof as defined above, or a pharmaceutical composition as defined above to said mammal. Alternatively, the present invention relates to an antibody or antigen-binding portion thereof as defined above, or a pharmaceutical composition as defined above for use in these methods. In a very preferred aspect of these embodiments, the mammal is a human patient.

All of the methods for treating a cancer according to the invention exclude a treatment of cancer-induced weight loss according to WO 2005/099746, WO 2009/021293 and Johnen H et al., Nature Medicine, 2007. This reflects the fact that according to these art teachings only cancer-induced weight loss can be reversed by anti-GDF-15 antibodies, and that growth of the cancer cannot be inhibited.

When taking into account the present invention, it becomes clear that the anti-GDF-15 antibodies known from WO 2005/099746, WO 2009/021293 and Johnen H et al., Nature Medicine, 2007 only inhibit one of the effects of human GDF-15 (i.e. cancer-induced weight loss), but fail to inhibit other effects of human GDF-15 such as those related to cancer growth.

The inhibition of cancer growth according to the present invention does not exclude that additional or secondary therapeutic benefits also occur in patients. For example, an additional or secondary benefit may be an influence on cancer-induced weight loss. However it is understood that the primary treatment for which protection is sought is for inhibiting cancer growth, any secondary or additional effects only reflect optional, additional advantages of the treatment of cancer growth.

In a preferred embodiment of the above methods, or antibodies, antigen-binding portions thereof or pharmaceutical compositions for use in these methods, the human patient has elevated GDF-15 levels in blood serum before administration. In a patient sub-group having elevated GDF-15 levels in blood serum, the treatment methods according to the invention are expected to be particularly effective at inhibiting cancer growth. In the most preferred aspect of this embodiment, GDF-15 levels are GDF-15 protein levels measured using the antibody according to the invention obtainable from the hybridoma cell line B1-23 deposited with the Deutsche Sammlung für Mikroorganismen and Zelikulturen GmbH (DSMZ) under the accession No. DSM ACC3142, preferably measured by immunochemistry.

In another embodiment of the above methods, or antibodies, antigen-binding portions thereof or pharmaceutical compositions for use in these methods, the antibody or antigen-binding portion thereof is the sole ingredient pharmaceutically active against cancer used in the method.

In an alternative embodiment of the above methods, or antibodies, antigen-binding portions thereof or pharmaceutical compositions for use in these methods, the antibody or antigen-binding portion thereof is used in combination with one or more further ingredients pharmaceutically active against cancer. In one aspect of this embodiment, the one or more further ingredients pharmaceutically active against cancer is a known anticancer agent and/or an immune-stimulatory molecule as defined above.

In a preferred embodiment of the above methods, or antibodies, antigen-binding portions thereof or pharmaceutical compositions for use in these methods, the cancer is selected from the group consisting of brain cancers including glioma, cancers of the nervous system, melanoma, lung cancer, lip and oral cavity cancer, hepatic carcinoma, leukemia, Hodgkin lymphoma, Non-Hodgkin lymphoma, bladder cancer, cervix uteri cancer, corpus uteri cancer, testis cancer, thyroid cancer, kidney cancer, gallbladder cancer, multiple myeloma, nasopharynx cancer, larynx cancer, pharynx cancer, esophagus cancer, gastrointestinal tumors including stomach and colorectal cancer, pancreatic cancer, prostate cancer, ovarian cancer and breast cancer, preferably from the group consisting of melanoma, prostate cancer, breast cancer, brain cancers including glioma, colorectal cancer, stomach cancer, esophagus cancer and ovarian cancer, and most preferably is melanoma. In one embodiment the cancer is selected from the above group, which further comprises endometrial cancer, such as endometrial carcinoma, breast cancer including subtypes of breast cancer, in particular triple-negative breast cancer and bladder cancer such as urothelial cell carcinoma.

In another preferred embodiment of the above methods, or antibodies, antigen-binding portions thereof or pharmaceutical compositions for use in these methods, the tumor or tumors formed by the cancer have higher human GDF-15 levels prior to administration compared to a control sample of the same patient obtained from a non-cancerous part of the tissue which is the tissue of origin of the cancer, preferably 1.2-fold higher levels, more preferably 1.5-fold higher levels, still more preferably 2-fold higher levels and most preferably 5-fold higher levels. In a patient sub-group having higher GDF-15 levels in the tumor or tumors formed by the cancer compared to the above control sample, the treatment methods according to the invention are expected to be particularly effective at inhibiting cancer growth.

In a very preferred embodiment of the above methods, or antibodies, antigen-binding portions thereof or pharmaceutical compositions for use in these methods, the method comprises inhibiting cancer growth. In a preferred aspect of this embodiment, cancer growth is stopped. In a more preferred aspect, the cancer shrinks.

In a preferred embodiment of the above methods, or antibodies, antigen-binding portions thereof or pharmaceutical compositions for use in these methods, the method comprises the induction of killing of cancer cells by NK cells and CD8+ T cells in the human patient. Due to their capability of preventing GDF-15 mediated down-regulation of the known immune surveillance regulator NKG2D, the antibodies or antigen-binding portions thereof according to the invention are expected to restore immune surveillance and induce the killing of cancer cells by NK cells and CD8+ T cells, in addition to effects of the antibodies or antigen-binding portions thereof that are independent of the immune system.

D) KITS

The present invention also provides kits comprising the pharmaceutical compositions as defined above.

In one embodiment, the kits are kits for use in the methods according to the invention as defined above.

In further embodiments, the present invention also provides a diagnostic kit comprising any of the antibodies or antigen-binding portions thereof according to the invention.

In one embodiment, the diagnostic kit may be used to detect whether the tumor or tumors of a cancer patient formed by the cancer have higher human GDF-15 levels compared to a control sample of the same patient obtained from a non-cancerous part of the tissue which is the tissue of origin of the cancer.

In another embodiment, the diagnostic kit may be used to detect whether a human cancer patient has elevated GDF-15 levels in blood serum.

E) SEQUENCES

The amino acid sequences referred to in the present application are as follows (in an N-terminal to C-terminal order; represented in the one-letter amino acid code):

SEQ ID No: 1 (Region of the Heavy Chain Variable Domain comprising an FR1, a CDR1, an FR2, a CDR2 and an FR3 region from the Polypeptide Sequence of monoclonal anti-human GDF-15 mAb-B1-23):

QVKLQQSGPGILQSSQTLSLTCSFSGFSLSTSGMGVSWIRQPSGKGLEW

LAHIYWDDDKRYNPTLKSRLTISKDPSRNQVFLKITSVDTADTATYYC

SEQ ID No: 2 (Region of the Light Chain Variable Domain comprising an FR1, a CDR1, an FR2, a CDR2 and an FR3 region from the Polypeptide Sequence of monoclonal anti-human GDF-15 mAb-B1-23):

DIVLTQSPKFMSTSVGDRVSVTCKASQNVGTNVAWFLQKPGQSPKALI

YSASYRYSGVPDRFTGSGSGTDFTLTISNVQSEDLAEYFC

SEQ ID No: 3 (Heavy Chain CDR1 Region Peptide Sequence of monoclonal anti-human GDF-15 mAb-B1-23):

GFSLSTSGMG

SEQ ID No: 4 (Heavy Chain CDR2 Region Peptide Sequence of monoclonal anti-human GDF-15 mAb-B1-23):

IYWDDDK

SEQ ID No: 5 (Heavy Chain CDR3 Region Peptide Sequence of monoclonal anti-human GDF-15 mAb-B1-23):

ARSSYGAMDY

SEQ ID No: 6 (Light Chain CDR1 Region Peptide Sequence of monoclonal anti-human GDF-15 mAb-B1-23):

QNVGTN

Light Chain CDR2 Region Peptide Sequence of monoclonal anti-human GDF-15 mAb-B1-23

SAS

SEQ ID No: 7 (Light Chain CDR3 Region Peptide Sequence of monoclonal anti-human GDF-15 mAb-B1-23):

QQYNNFPYT

SEQ ID No: 8 (recombinant mature human GDF-15 protein):

GSARNGDHCPLGPGRCCRLHTVRASLEDLGWADWVLSPREVQVTMCIGA

CPSQFRAANMHAQIKTSLHRLKPDTVPAPCCVPASYNPMVLIQKTDTGV

SLQTYDDLLAKDCHCI

SEQ ID No: 9 (human GDF-15 precursor protein):

MPGQELRTVNGSQMLLVLLVLSWLPHGGALSLAEASRASFPGPSELHSED

SRFRELRKRYEDLLTRLRANQSWEDSNTDLVPAPAVRILTPEVRLGSGG

HLHLRISRAALPEGLPEASRLHRALFRLSPTASRSWDVTRPLRRQLSLA

RPQAPALHLRLSPPPSQSDQLLAESSSARPQLELHLRPQAARGRRRAR

ARNGDHCPLGPGRCCRLHTVRASLEDLGWADWVLSPREVQVTMCIGAC

PSQFRAANMHAQIKTSLHRLKPDTVPAPCCVPASYNPMVLIQKTDTGVS

LQTYDDLLAKDCHCI

SEQ ID No: 10 (human GDF-15 precursor protein+N-terminal and C-terminal GSGS linker):

GSGSGSGMPGQELRTVNGSQMLLVLLVLSWLPHGGALSLAEASRASFPG

PSELHSEDSRFRELRKRYEDLLTRLRANQSWEDSNTDLVPAPAVRILTPE

VRLGSGGHLHLRISRAALPEGLPEASRLHRALFRLSPTASRSWDVTRPL

RRQLSLARPQAPALHLRLSPPPSQSDQLLAESSSARPQLELHLRPQAA

RGRRRARARNGDHCPLGPGRCCRLHTVRASLEDLGWADWVLSPREVQV

TMCIGACPSQFRAANMHAQIKTSLHRLKPDTVPAPCCVPASYNPMVLIQK

TDTGVSLQTYDDLLAKDCHCIGSGSGSG

SEQ ID No: 11 (Flag peptide):

DYKDDDDKGG

SEQ ID No: 12 (HA peptide):

YPYDVPDYAG

SEQ ID No: 13 (peptide derived from human GDF-15):

ELHLRPQAARGRR

SEQ ID No: 14 (peptide derived from human GDF-15):

LHLRPQAARGRRR

SEQ ID No: 15 (peptide derived from human GDF-15):

HLRPQAARGRRRA

SEQ ID No: 16 (peptide derived from human GDF-15):

```
LRPQAARGRRRAR
```

SEQ ID No: 17 (peptide derived from human GDF-15):

```
RPQAARGRRRARA
```

SEQ ID No: 18 (peptide derived from human GDF-15):

```
PQAARGRRRARAR
```

SEQ ID No: 19 (peptide derived from human GDF-15):

```
QAARGRRRARARN
```

SEQ ID No: 20 (peptide derived from human GDF-15):

```
MHAQIKTSLHRLK
```

SEQ ID No: 25 (GDF-15 peptide comprising part of the GDF-15 Epitope that binds to B1-23):

```
EVQVTMCIGACPSQFR
```

SEQ ID No: 26 (GDF-15 peptide comprising part of the GDF-15 Epitope that binds to B1-23):

```
TDTGVSLQTYDDLLAKDCHCI
```

The nucleic acid sequences referred to in the present application are as follows (in a 5' to 3' order; represented in accordance with the standard nucleic acid code):

SEQ ID No: 21 (DNA nucleotide sequence encoding the amino acid sequence defined in SEQ ID No: 1):

```
CAAGTGAAGCTGCAGCAGTCAGGCCCTGGGATATTGCAGTCCTCCCAGAC
CCTCAGTCTGACTTGTTCTTTCTCTGGGTTTTCACTGAGTACTTCTGGTA
TGGGTGTGAGCTGGATTCGTCAGCCTTCAGGAAAGGGTCTGGAGTGGCTG
GCACACATTTACTGGGATGATGACAAGCGCTATAACCCAACCCTGAAGAG
CCGGCTCACAATCTCCAAGGATCCCTCCAGAAACCAGGTATTCCTCAAGA
TCACCAGTGTGGACACTGCAGATACTGCCACATACTACTGT
```

SEQ ID No: 22 (DNA nucleotide sequence encoding the amino acid sequence defined in SEQ ID No: 2):

```
GACATTGTGCTCACCCAGTCTCCAAAATTCATGTCCACATCAGTAGGAGA
CAGGGTCAGCGTCACCTGCAAGGCCAGTCAGAATGTGGGTACTAATGTGG
CCTGGTTTCTACAGAAACCAGGGCAATCTCCTAAAGCACTTATTTACTCG
GCATCCTACCGGTACAGTGGAGTCCCTGATCGCTTCACAGGCAGTGGATC
TGGGACAGATTTCACTCTCACCATCAGCAACGTGCAGTCTGAAGACTTGG
CAGAGTATTTCTGT
```

SEQ ID No: 23 (DNA nucleotide sequence encoding the amino acid sequence defined in SEQ ID No: 5):

```
GCTCGAAGTTCCTACGGGGCAATGGACTAC
```

SEQ ID No: 24 (DNA nucleotide sequence encoding the amino acid sequence defined in SEQ ID No: 7):

```
CAGCAATATAACAACTTTCCGTACACG
```

F) EXAMPLES

The present invention is illustrated by the following non-limiting Examples:

Example 1: Generation and Characterization of the GDF-15 Antibody B1-23

The antibody B1-23 was generated in a GDF-15 knock out mouse. Recombinant human GDF-15 (SEQ ID No: 8) was used as the immunogen.

The hybridoma cell line B1-23 producing mAb-B1-23 was deposited with the Deutsche Sammlung für Mikroorganismen and Zellkulturen GmbH (DMSZ) under the accession No. DSM ACC3142, in accordance with the Budapest Treaty.

By means of a commercially available test strip system, B1-23 was identified as an IgG2a (kappa chain) isotype. Using surface plasmon resonance measurements, the dissociation constant (Kd) was determined as follows:

Binding of the monoclonal anti-human-GDF-15 antibody anti-human GDF-15 mAb-B1-23 according to the invention was measured by employing surface plasmon resonance measurements using a Biorad ProteOn XPR36 system and Biorad G L C sensor chips:

For preparing the biosensors recombinant mature human GDF-15 protein was immobilized on flow cells 1 and 2. On one flow cell recombinant GDF-15 derived from Baculvirus-transfected insect cells (HighFive insect cells) and on the other recombinant protein derived from expression in E. coli was used. The GLC sensor chip was activated using Sulfo-NHS (N-Hydroxysulfosuccinimide) and EDC (1-Ethyl-3-[3-dimethylaminopropyl]carbodiimide hydrochloride) (Biorad ProteOn Amine Coupling Kit) according to the manufacturer's recommendation, the sensor surface was subsequently loaded with the proteins up to a density of about 600 RU (1Ru=1 pg mm$^{-2}$). The non-reacted coupling groups were then quenched by perfusion with 1M ethanolamine pH 8.5 and the biosensor was equilibrated by perfusing the chip with running buffer (10M HEPES, 150 mM NaCl, 3.4 mM EDTA, 0.005% Tween-20, pH 7.4, referred to as HBS150). As controls two flow cells were used, one empty with no protein coupled and one coupled with an non-physiological protein partner (human Interleukin-5), which was immobilized using the same coupling chemistry and the same coupling density. For interaction measurements anti-human GDF-15 mAb-B1-23 was dissolved in HBS150 and used in six different concentrations as analyte (concentration: 0.4, 0.8, 3, 12, 49 and 98 nM). The analyte was perfused over the biosensor using the one-shot kinetics setup to avoid intermittent regeneration, all measurements were performed at 25° C. and using a flow rate of 100 µl min$^{-1}$. For processing the bulk face effect and unspecific binding to the sensor matrix was removed by subtracting the SPR data of the empty flow cell (flow cell 3)

from all other SPR data. The resulting sensogram was analyzed using the software ProteOn Manager version 3.0. For analysis of the binding kinetics a 1:1 Langmuir-type interaction was assumed. For the association rate constant a value of $5.4\pm0.06\times10^5$ $M^{-1}s^{-1}$ ($k_{on}$) and for the dissociation rate constant a value of $4.3\pm0.03\times10^{-4}$ $s^{-1}$ ($k_{off}$) could be determined (values are for the interaction of anti-human GDF-15 mAb-B1-23 with GDF-15 derived from insect cell expression). The equilibrium dissociation constant was calculated using the equation $K_D=k_{off}/k_{on}$ to yield a value of about 790 pM. Affinity values for the interaction of GDF-15 derived from E. coli expression and the anti-human GDF-15 mAb-B1-23 differ by less than a factor of 2, rate constants for GDF-15 derived from insect cells and E. coli deviate by about 45% and are thus within the accuracy of SPR measurements and likely do not reflect a real difference in affinity. Under the conditions used the anti-human GDF-15 mAb-B1-23 shows no binding to human interleukin-5 and thus confirms the specificity of the interaction data and the anti-human GDF-15 mAb-B1-23.

The amino acid sequence of recombinant human GDF-15 (as expressed in Baculovirus-transfected insect cells) is:

```
                                          (SEQ ID No: 8)
GSARNGDHCP LGPGRCCRLH TVRASLEDLG WADWVLSPRE

VQVTMCIGAC PSQFRAANMH AQIKTSLHRL KPDTVPAPCC

VPASYNPMVL IQKTDTGVSL QTYDDLLAKD CHCI
```

Thus, using surface plasmon resonance measurements, the dissociation constant (Kd) of 790 pM was determined. As a comparison: the therapeutically used antibody Rituximab has a significantly lower affinity (Kd=8 nM).

Example 2: Antagonization of GDF-15 Mediated Effects with mAB B1-23 a) The NKG2D (Natural Killer Group 2D) receptor, which is expressed on NK cells and CD8+ T cells, is known to play an important role in the immune surveillance against tumors. Transformed as well as viral infected cells express ligands, which bind to the NKG2D receptor, thereby activating the cytotoxic effector functions of the described immune cells. In that way transformed cells can be detected and eliminated by the immune system. After treatment of immune cells with either recombinant human GDF-15 or tumor cell secreted GDF-15 in vitro for 72 hours, the expression level of NKG2D on the cell surface of lymphocytes was downregulated (FIG. 1). After 72 hours incubation the immune cells were stained with the following FACS-antibodies: anti CD3, anti CD56, anti-NKG2D. Using this antibody combination, the experiment focused on NK cells and their NKG2D surface expression. The low NKG2D level on immune cells led to an impaired tumor/target cell lysis. The GDF-15 mediated downregulation of NKG2D was prevented by mAb B1-23.

Figure 2:
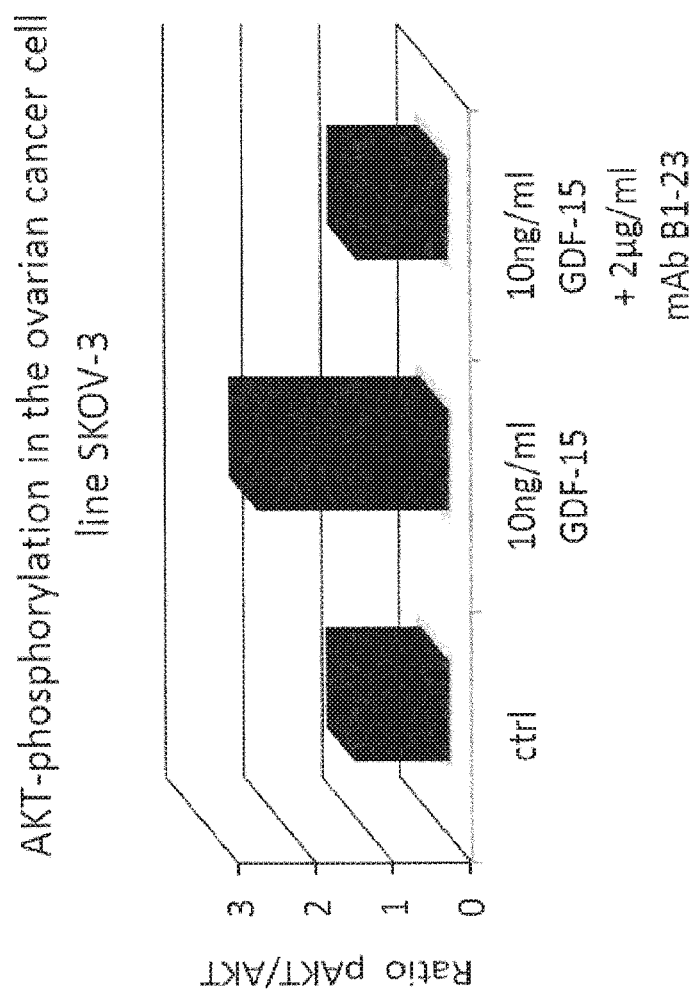
FIG. 2: Akt Phosphorylation in the Ovarian Carcinoma Cell Line SK-OV-3. In order to quantify the Western Blot for the ovarian carcinoma cell line SK-OV-3, the ratio of phosphorylated Akt to the total amount of Akt was calculated and normalized to the untreated control.
Figure 3:
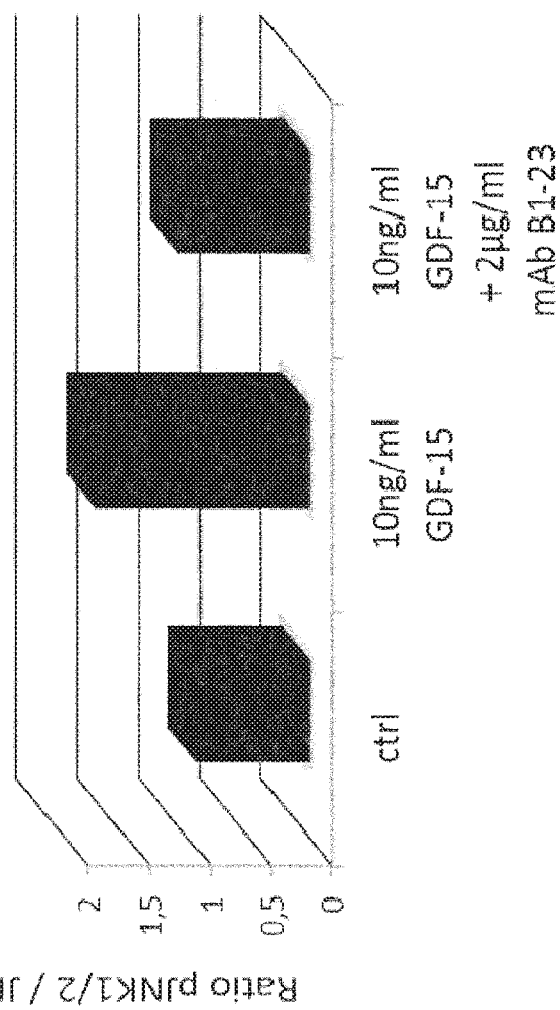
FIG. 3: JNK1/2 Phosphorylation in Immune Cells. In order to quantify the Western Blot, the ratio of phosphorylated JNK1/2 to the total amount of JNK was calculated and normalized to the untreated control.

It is therefore concluded that human GDF-15 downregulates expression of NKG2D on the cell surface of lymphocytes and thereby downregulates immune surveillance against tumors. By binding to human GDF-15, the antibodies of the present invention are capable of preventing GDF-15 mediated downregulation of NKG2D and should be capable of restoring immune surveillance and inducing the killing of cancer cells by NK cells and CD8+ T cells.

b) The treatment of the ovarian cancer cell line SK-OV-3 with recombinant GDF-15 led to the phosphorylation of AKT. AKT is a molecule, which is part of the PI3K-pathway and contributes to the activation and proliferation of cells. In this experiment SK-OV-3 cells were treated with 10 ng/ml recombinant GDF-15 for 10 min at 37° C., 5% CO2. 5 minutes preincubation of 2 µg mAb-B1-23 with 10 ng/ml GDF-15 at 37° C. blocked the GDF-15 mediated AKT-phosphorylation (FIG. 2). This showed the neutralizing effect of mAb-B1-23.

c) Treatment of immune cells with recombinant GDF-15 led to the phosphorylation of JNK, a kinase, which is activated either by cytokines or by stress. Antagonization of 10 ng/ml GDF-15 with 2 µg mAb-B1-23 (5 minute preincubation at 37°) blocked the GDF-15 mediated JNK1/2-phosphorylation (FIG. 3).

Example 3: Inhibition of Cancer Cell Proliferation Using mAb B1-23

Data generated with B1-23 showed an antiproliferative effect of the antibody on cancer cells in vitro. The strongest antiproliferative effect was observed using the prostate cancer cell line LnCap, which produces lots of GDF-15. A metabolic assay (Alamar Blue assay) showed a decrease of proliferation of 30% after 72 hrs when mAb-B1-23 was present, compared with the control group, where the antibody was not applied. Since cytotoxic effects of the antibody have been excluded in different assays, this effect proves a significantly decreased cell division rate after blockade of GDF-15.

Example 4: mAb B1-23 Inhibits Growth of Tumors In Vivo

In one experimental study setup, tumor growth is studied in a SK-Mel28 human melanoma cell model in immunodeficient NMRI mice. $7.5\times10^6$ melanoma cells are implanted subcutaneously into each mouse. On day 23 after inoculation (i.e. during the exponential growth phase of the malignoma), the mAb B1-23 antibody is administered for the first time. After injection of mAb B1-23 (30 mg/kg body weight i.p.), no further tumor growth is observed in the mAb B1-23-treated mice for one week, whereas the tumors in the negative control samples continue growing.

This Example demonstrates that the mAb B1-23 antibody of the present invention inhibits cancer growth in mice bearing tumors derived from human cells.

Because this example uses human melanoma cells, the anti-human GDF-15 antibodies of the present invention should also inhibit cancer growth in a human patient. Inhibition of cancer growth should be particularly effective if the patient has elevated GDF-15 levels in blood serum before administration, or if the tumor or tumors formed by the cancer have higher human GDF-15 levels compared to a control sample of the same patient obtained from a non-cancerous part of the tissue which is the tissue of origin of the cancer.

The present Example uses immunodeficient mice. It is therefore concluded that the antibodies of the present invention are capable of inhibiting cancer growth in a manner that is independent of an intact immune system.

In addition, it was shown above in Example 2 that the anti-human GDF-15 antibodies of the present invention are capable of preventing GDF-15 mediated downregulation of NKG2D and should be capable of inducing the killing of cancer cells by NK cells and CD8+ T cells. It is therefore expected that cancer growth inhibition by anti-human GDF-15 antibodies is stronger in patients than in the immunodeficient mice, since the patients do not have the immune deficiencies of the mice used in the present Example.

In an alternative experimental study setup, the following in vivo study was carried out:

To assess an anti-tumor effect of B1-23 in vivo, Balb/c$^{nu/nu}$ nude mice were used in a xenograft setting with the melanoma cell line UACC-257. The mice were treated either with the antibody B1-23 or with PBS. Each treatment cohort contained 10 Balb/c$^{nu/nu}$ nude mice.

Prior to injection, the UACC-257 melanoma cells were grown in complete medium, excluding any contamination. The cells were harvested when 70-80% confluence was reached in the cell culture flask. Cells were then washed with PBS and counted. 1×10$^7$ viable cells were suspended in PBS.

The first injection/treatment was administered in 6 week old Balb/c$^{nu/nu}$ nude mice. The inoculation area of the mice was cleaned with ethanol. The UACC 257 cells were mixed and drawn into a syringe without a needle, in order to avoid negative pressure on the tumor cells. The cell suspension containing 1×10$^7$ cells in PBS was injected subcutaneously (s.c.) into the lower flank of the mice.

The intraperitoneal (i.p.) injection of either B1-23 (25 mg/kg body weight) or the same volume of PBS started immediately after the tumor cell inoculation (defined as day 1) and was administered twice a week. The tumors were grown for 48 days. The tumor diameters were measured with a caliper and the tumor volume in mm3 was calculated by the formula:

Volume=(width)$^2$×length/2

Figure 4:
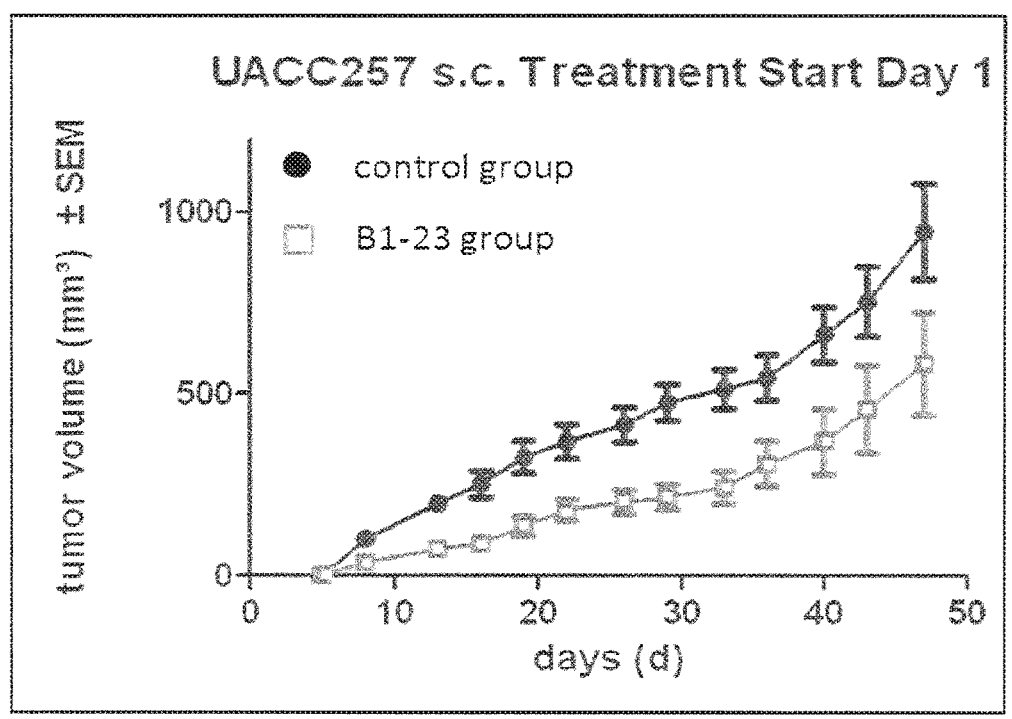
FIG. 4.

The results which were obtained from the study are shown in FIG. 4.

As demonstrated in the Figure, the tumor size of the animal cohort treated with B1-23 was significantly decreased, compared to the PBS control group.

Example 5: mAb B1-23 Recognizes a Conformational or a Discontinuous Epitope of Human GDF-15

Epitope Mapping: Monoclonal mouse antibody GDF-15 against 13mer linear peptides derived from GDF-15
Antigen: GDF-15:

```
(322 amino acids with linker)
                                     (SEQ ID No: 10)
GSGSGSGMPGQELRTVNGSQMLLVLLVLSWLPHGGALSLAEASRASFPGP

SELHSEDSRFRELRKRYEDLLTRLRANQSWEDSNTDLVPAPAVRILTPEV

RLGSGGHLHLRISRAALPEGLPEASRLHRALFRLSPTASRSWDVTRPLRR

QLSLARPQAPALHLRLSPPPSQSDQLLAESSSARPQLELHLRPQAARGRR

RARARNGDHCPLGPGRCCRLHTVRASLEDLGWADWVLSPREVQVTMCIGA

CPSQFRAANMHAQIKTSLHRLKPDTVPAPCCVPASYNPMVLIQKTDTGVS

LQTYDDLLAKDCHCIGSGSGSG
```

The protein sequence was translated into 13mer peptides with a shift of one amino acid. The C- and N-termini were elongated by a neutral GSGS linker to avoid truncated peptides (bold letters).

Control Peptides:
Flag: DYKDDDDKGG (SEQ ID No:13), 78 spots; HA: YPYDVPDYAG (SEQ ID No:14), 78 spots (each array copy)

Peptide Chip Identifier:
000264_01 (10/90, Ala2Asp linker)
Staining Conditions:
Standard buffer: PBS, pH 7.4+0.05%; Tween 20
Blocking buffer: Rockland blocking buffer MB-070
Incubation buffer: Standard buffer with 10% Rockland blocking buffer MB-070
Primary sample: Monoclonal mouse antibody GDF-15 (1 µg/µl): Staining in incubation buffer for 16 h at 4° C. at a dilution of 1:100 and slight shaking at 500 rpm
Secondary antibody: Goat anti-mouse IgG (H+L) IRDye680, staining in incubation buffer with a dilution of 1:5000 for 30 min at room temperature (RT)
Control antibodies: Monoclonal anti-HA (12CA5)-LL-Atto 680 (1:1000), monoclonal anti-FLAG(M2)-Fluo-Probes752 (1:1000); staining in incubation buffer for 1 h at RT
Scanner:
Odyssey Imaging System, LI-COR Biosciences
Settings: offset: 1 mm; resolution: 21 µm; intensity green/red: 7/7
Results:
After 30 min pre-swelling in standard buffer and 30 min in blocking buffer, the peptide array with 10, 12 and 15mer B7H3-derived linear peptides was incubated with secondary goat anti-mouse IgG (H+L) IRDye680 antibody only at a dilution of 1:5000 for 1 h at room temperature to analyze background interactions of the secondary antibody. The PEPperCHIP® was washed 2×1 min with standard buffer, rinsed with dist. water and dried in a stream of air. Read-out was done with Odyssey Imaging System at a resolution of 21 µm and green/red intensities of 7/7: We observed a weak interaction of arginine-rich peptides (ELHLRPQAARGRR (SEQ ID No:15), LHLRPQAARGRRR (SEQ ID No:16), HLRPQAARGRRRA (SEQ ID No:17), LRPQAARGRRRAR (SEQ ID No:18), RPQAARGRRRARA (SEQ ID No:19), PQAARGRRRARAR (SEQ ID No:20) and QAARGRRRARARN (SEQ ID No:21)) that are known as frequent binders, and with the basic peptide MHAQIKTSLHRLK (SEQ ID No:22) due to ionic interactions with the charged antibody dye.

After pre-swelling for 10 min in standard buffer, the peptide microarray was incubated overnight at 4° C. with monoclonal mouse antibody GDF-15 at a dilution of 1:100. Repeated washing in standard buffer (2×1 min) was followed by incubation for 30 min with the secondary antibody at a dilution of 1:5000 at room temperature. After 2×10 sec. washing in standard buffer and short rinsing with dist. water, the PEPperCHIP® was dried in a stream of air. Read-out was done with Odyssey Imaging System at a resolution of 21 µm and green/red intensities of 7/7 before and after staining of control peptides by anti-HA and anti-FLAG(M2) antibodies.

It was shown that none of the linear 13mer peptides derived from GDF-15 interacted with monoclonal mouse antibody GDF-15 even at overregulated intensities. Staining of Flag and HA control peptides that frame the array, however, gave rise to good and homogeneous spot intensities.

SUMMARY

The Epitope Mapping of monoclonal mouse GDF-15 antibody against GDF-15 did not reveal any linear epitope with the 13mer peptides derived from the antigen. According to this finding it is very likely that monoclonal mouse antibody GDF-recognizes a conformational or a discontinuous epitope with low affinity of partial epitopes. Due to the obvious absence of any GDF-15 signal above the background staining of the secondary antibody only, quantification of spot intensities with PepSlide® Analyzer and subsequent peptide annotation were omitted.

Example 6: Structural Identification of Peptide Ligand Epitopes by Mass Spectrometric Epitope Excision and Epitope Extraction The epitope of recombinant human GDF-15 which binds to the antibody B1-23 was identified by means of the epitope excision method and epitope extraction method (Suckau et al. Proc Natl Acad Sci USA. 1990 December; 87(24): 9848-9852; R. Stefanescu et al., Eur. J. Mass Spectrom. 13, 69-75 (2007)).

For preparation of the antibody column, the antibody B1-23 was added to NHS-activated 6-aminohexanoic acid coupled sepharose. The sepharose-coupled antibody B1-23 was then loaded into a 0.8 ml microcolumn and washed with blocking and washing buffers.

Epitope Extraction Experiment:

Recombinant human GDF-15 was digested with trypsin for 2 h at 37° C. (in solution), resulting in different peptides, according to the trypsin cleavage sites in the protein. After complete digestion, the peptides were loaded on the affinity column containing the immobilized antibody B1-23. Unbound as well as potentially bound peptides of GDF-15 were used for mass spectrometry analysis. An identification of peptides by means of mass spectrometry was not possible. This was a further indicator that the binding region of GDF-15 in the immune complex B1-23 comprises a discontinuous or conformational epitope. In case of a continuous linear epitope, the digested peptides should bind its interaction partner, unless there was a trypsin cleavage site in the epitope peptide. A discontinuous or conformational epitope could be confirmed by the epitope excision method described in the following part.

Epitope Excision Experiment:

The immobilized antibody B1-23 on the affinity column was then incubated with recombinant GDF-15 for 2 h. The formed immune complex on the affinity column was then incubated with trypsin for 2 h at 37° C. The cleavage resulted in different peptides derived from the recombinant GDF-15. The immobilized antibody itself is proteolytically stable. The resulting peptides of the digested GDF-15 protein, which were shielded by the antibody and thus protected from proteolytic cleavage, were eluted under acidic conditions (TFA, pH2), collected and identified by mass spectrometry.

The epitope excision method using MS/MS identification resulted in the following peptides:

| Peptide | Position in sequence | Mass | Ion/Charge |
|---|---|---|---|
| EVQVTMCIGACPSQFR (SEQ ID No: 25) | 40-55 | 1769.91 | 590.50(3+) |
| TDTGVSLQTYDDLLAKDCHCI (SEQ ID No: 26) | 94-114 | 2310.96 | 771:33(3+) |

The part of human GDF-15, which binds the antibody B1-23, comprises a discontinuous or conformational epitope. Mass spectrometry identified 2 peptides in the GDF-15 protein, which are responsible for the formation of the immune complex. These peptides are restricted to the positions 40-(EVQVTMCIGACPSQFR) and 94-114 (TDTGVSLQTYDDLLAKDCHCI) in the GDF-15 amino acid sequence. Thus, these two peptides comprise an epitope of the GDF-15 protein that binds to the antibody B1-23.

G) INDUSTRIAL APPLICABILITY

The antibodies, antigen-binding portions thereof, pharmaceutical compositions and kits according to the present invention may be industrially manufactured and sold as products for the claimed methods and uses (e.g. for treating cancer), in accordance with known standards for the manufacture of pharmaceutical products. Accordingly, the present invention is industrially applicable.

REFERENCES

Arbabi Ghahroudi M et al.: "Selection and identification of single domain antibody fragments from camel heavy-chain antibodies." FEES Lett. 1997 Sep. 15; 414(3):521-6.

Ausubel et al.: "Current Protocols in Molecular Biology." Greene Publishing Associates and Wiley Interscience; New York 1992.

Bauskin A R et al.: "The propeptide mediates formation of stromal stores of PROMIC-1: role in determining prostate cancer outcome." Cancer Res. 2005 Mar. 15; 65(6):2330-6.

Brown D A et al.: "Macrophage inhibitory cytokine 1: a new prognostic marker in prostate cancer." Clin Cancer Res. 2009 Nov. 1; 15(21):6658-64.

Chothia C et al.: Conformations of immunoglobulin hyper-variable regions. Nature. 1989 Dec. 21-28; 342(6252): 877-83.

Clackson T et al.: "Making antibody fragments using-phage display libraries." Nature. 1991 Aug. 15; 352(6336):624-8.

Giudicelli V et al.: IMGT/V-QUEST, an integrated software program for immunoglobulin and T cell receptor V-J and V-D-J rearrangement analysis. Nucleic Acids Res. 2004 Jul. 1; 32 (Web Server issue):W435-40.

Harlow and Lane: "Antibodies: A Laboratory Manual" Cold Spring Harbor Laboratory Press, Cold Spring Harbor, N.Y. 1988.

Holliger P et al.: ""Diabodies": small bivalent and bispecific antibody fragments." Proc Natl Acad Sci USA. 1993 Jul. 15; 90(14):6444-8.

Holt L J et al.: "Domain antibodies: proteins for therapy." Trends Biotechnol. 2003 November; 21(11):484-90.

Huang C Y et al.: "Molecular alterations in prostate carcinomas that associate with in vivo exposure to chemotherapy: identification of a cytoprotective mechanism involving growth differentiation factor 15." Clin Cancer Res. 2007 Oct. 1; 13(19):5825-33.

Johnen E et al.: "Tumor-induced anorexia and weight loss are mediated by the TGF-beta superfamily cytokine MIC-1." Nat Med. 2007 November; 13(11):1333-40.

Jones P T et al.: "Replacing the complementarity-determining regions in a human antibody with those from a mouse." Nature. 1986 May 29-Jun. 4; 321(6069):522-5.

Kabat et al.: Sequences of proteins of immunological interest, U.S. Dept. of Health and Human Services, Public Health Service, National Institutes of Health, Bethesda, Md. 1983.

Köhler G and Milstein C: "Continuous cultures of fused cells secreting antibody of predefined specificity." Nature. 1975 Aug. 7; 256(5517):495-7.

Marks J D et al.: "By-passing immunization. Human antibodies from V-gene libraries displayed on phage." J Mol Biol. 1991 Dec. 5; 222(3):581-97.

Mimeault M and Batra S K: "Divergent molecular mechanisms underlying the pleiotropic functions of macrophage inhibitory cytokine-1 in cancer." J Cell Physiol. 2010 September; 224(3):626-35.

Paul, W. E. (Ed.): "Fundamental Immunology" 2nd Ed. Raven Press, Ltd., New York 1989.

Remington's Pharmaceutical Sciences, Ed. A R Gennaro, 20th edition, 2000, Williams & Wilkins, Pa., USA.

Riechmann L et al.: "Reshaping human antibodies for therapy." Nature. 1988 Mar. 24; 332(6162):323-7.

Roth P et al.: "GDF-15 contributes to proliferation and immune escape of malignant gliomas." Clin Cancer Res. 2010 Aug. 1; 16(15):3851-9.

Saerens D et al.: "Single-domain antibodies as building blocks for novel therapeutics." Curr Opin Pharmacol. 2008 October; 8(5):600-8. Epub 2008 Aug. 22.

Sambrook et al.: "Molecular Cloning: A Laboratory Manual.", 2nd Ed., Cold Spring Harbor Laboratory Press, Cold Spring Harbor, N.Y. 1989.

Siegel D L: "Recombinant monoclonal antibody technology." Transfus Clin Biol. 2002 January; 9(1):15-22.

Stefanescu R. et al., Eur. J. Mass Spectrom. 13, 69-75 (2007)

Suckau et al. Proc Natl Acad Sci USA. 1990 December; 87(24): 9848-9852.

Weinberg R. et al.: The Biology of Cancer. Garland Science: New York 2006. 850p.

WO 2005/099746

WO 2009/021293

PREFERRED EMBODIMENTS

1. A monoclonal antibody capable of binding to human GDF-15, or an antigen-binding portion thereof, wherein the heavy chain variable domain comprises a CDR3 region comprising the amino acid sequence of SEQ ID NO: 5 or an amino acid sequence at least 90% identical thereto, and wherein the light chain variable domain comprises a CDR3 region comprising the amino acid sequence of SEQ ID NO: 7 or an amino acid sequence at least 85% identical thereto.

2. The monoclonal antibody or antigen-binding portion thereof according to item 1, wherein the heavy chain variable domain comprises a CDR3 region comprising the amino acid sequence of SEQ ID NO: 5, or wherein the light chain variable domain comprises a CDR3 region comprising the amino acid sequence of SEQ ID NO: 7.

3. The monoclonal antibody or antigen-binding portion thereof according to item 1 or 2, wherein the heavy chain variable domain comprises a CDR3 region comprising the amino acid sequence of SEQ ID NO: 5, and wherein the light chain variable domain comprises a CDR3 region comprising the amino acid sequence of SEQ ID NO: 7.

4. The monoclonal antibody or antigen-binding portion thereof according to any one of items 1 to 3, wherein the heavy chain variable domain comprises a region comprising an FR1, a CDR1, an FR2, a CDR2 and an FR3 region and comprising the amino acid sequence of SEQ ID NO: 1 or a sequence 95% identical thereto, and wherein the light chain variable domain comprises a region comprising an FR1, a CDR1, an FR2, a CDR2 and an FR3 region and comprising the amino acid sequence of SEQ ID NO: 2 or a sequence 95% identical thereto.

5. The monoclonal antibody or antigen-binding portion thereof according to any one of items 1 to 4, wherein the heavy chain variable domain comprises a region comprising an FR1, a CDR1, an FR2, a CDR2 and an FR3 region and comprising the amino acid sequence of SEQ ID NO: 1 or a sequence 98% identical thereto, and wherein the light chain variable domain comprises a region comprising an FR1, a CDR1, an FR2, a CDR2 and an FR3 region and comprising the amino acid sequence of SEQ ID NO: 2 or a sequence 98% identical thereto.

6. The monoclonal antibody or antigen-binding portion thereof according to any one of items 1 to 5, wherein the antibody or antigen-binding portion thereof has an equilibrium dissociation constant for human GDF-15 that is equal to or less than 20 nM, preferably less than 10 nM, more preferably less than 5 nM and most preferably between 0.1 nM and 2 nM.

7. The monoclonal antibody or antigen-binding portion thereof according to any one of items 1 to 6, wherein the antibody or antigen-binding portion thereof binds to the same human GDF-15 epitope as the antibody to human GDF-15 obtainable from the cell line B1-23 deposited with the Deutsche Sammlung für Mikroorganismen und Zellkulturen GmbH (DMSZ) under the accession No. DSM ACC3142.

8. The monoclonal antibody or antigen-binding portion thereof according to any one of items 1 to 7, wherein the antibody is the antibody to human GDF-15 obtainable from the cell line B1-23 deposited with the Deutsche Sammlung für Mikroorganismen und Zellkulturen GmbH (DMSZ) under the accession No. DSM ACC3142 or an antigen-binding portion thereof.

9. The monoclonal antibody or antigen-binding portion thereof of any one of items 1-8, wherein the antibody is capable of inhibiting cancer growth in a mammal, preferably a human patient.

10. The monoclonal antibody or antigen-binding portion thereof of any one of items 1-9, wherein the human GDF-15 is recombinant human GDF-15 having the amino acid sequence represented by SEQ ID No: 8.

11. The monoclonal antibody or antigen-binding portion thereof of any one of items 1-10, wherein the binding is binding to a conformational or discontinuous epitope on human GDF-15.

12. The monoclonal antibody or antigen-binding portion thereof of item 11, wherein the binding to a conformational or discontinuous epitope on human GDF-15 is binding to a conformational or discontinuous epitope comprised by the amino acid sequences of SEQ ID No: 25 and SEQ ID No: 26.

13. A monoclonal antibody capable of binding to human GDF-15, or an antigen-binding portion thereof, wherein the binding is binding to a conformational or discontinuous epitope on human GDF-15 comprised by the amino acid sequences of SEQ ID No: 25 and SEQ ID No: 26.

14. The monoclonal antibody or antigen-binding portion thereof of item 13, wherein the antibody or antigen-binding portion thereof is an antibody or antigen-binding portion thereof as defined in any one of items 1-10.

15. A pharmaceutical composition comprising the antibody or antigen-binding portion thereof according to any one of items 1 to 14.

16. An antibody or antigen-binding portion thereof according to any one of items 1 to 14 or a pharmaceutical composition according to item 15 for use in a method for treating cancer in a mammal, the method comprising administering the antibody or antigen-binding portion thereof or the pharmaceutical composition to said mammal.

17. The antibody or antigen-binding portion thereof or the pharmaceutical composition according to item 16 for the use according to item 16, wherein the mammal is human patient.

18. The antibody or antigen-binding portion thereof or the pharmaceutical composition according to item 17 for the use according to item 17, wherein the human patient has elevated GDF-15 levels in blood serum before administration.

19. The antibody or antigen-binding portion thereof or the pharmaceutical composition according to any one of items 16 to 18 for the use according to any one of items 16 to 18, wherein the antibody or antigen-binding portion thereof is
    A) the sole ingredient pharmaceutically active against cancer used in the method, or
    B) used in combination with one or more further ingredients pharmaceutically active against cancer.

20. The antibody or antigen-binding portion thereof or the pharmaceutical composition according to any one of items 16 to 19 for the use according to any one of items 16 to 19, wherein the cancer is selected from the group consisting of brain cancers including glioma, cancers of the nervous system, melanoma, lung cancer, lip and oral cavity cancer, hepatic carcinoma, leukemia, Hodgkin lymphoma, Non-Hodgkin lymphoma, bladder cancer, cervix uteri cancer, corpus uteri cancer, testis cancer, thyroid cancer, kidney cancer, gallbladder cancer, multiple myeloma, nasopharynx cancer, larynx cancer, pharynx cancer, esophagus cancer, gastrointestinal tumors including stomach and colorectal cancer, pancreatic cancer, prostate cancer, ovarian cancer and breast cancer, preferably from the group consisting of melanoma, prostate cancer, breast cancer, brain cancers including glioma, colorectal cancer, stomach cancer, esophagus cancer and ovarian cancer, and most preferably is melanoma.

21. The antibody or antigen-binding portion thereof or the pharmaceutical composition according to any one of items 17 to 20 for the use according to any one of items 17 to 20, wherein prior to administration, the tumor or tumors formed by the cancer have higher human GDF-15 levels compared to a control sample of the same patient obtained from a non-cancerous part of the tissue which is the tissue of origin of the cancer, preferably 1.2-fold higher levels, more preferably 1.5-fold higher levels, still more preferably 2-fold higher levels and most preferably 5-fold higher levels.

22. itemitemThe antibody or antigen-binding portion thereof or the pharmaceutical composition according to any one of items 16 to 21 for the use according to any one of items 16 to 21, wherein the method comprises inhibiting cancer growth.

23. The antibody or antigen-binding portion thereof or the pharmaceutical composition according to any one of items 17 to 22 for the use according to any one of items 17 to 22, wherein the method comprises the induction of killing of cancer cells by NK cells and CD8+ T cells in the human patient.

24. A kit comprising the pharmaceutical composition of item 15.

25. The kit of item 24 for a use according to any one of items 16 to 23.

26. An expression vector comprising a nucleotide sequence encoding the antibody or antigen-binding portion thereof according to any of items 1-14.

27. A cell line capable of producing an antibody or antigen-binding portion thereof according to any one of items 1 to 14.

28. The cell line according to item 27, wherein the cell line is the cell line B1-23 deposited with the Deutsche Sammlung für Mikroorganismen and Zellkulturen GmbH (DMSZ) under the accession No. DSM ACC3142.

29. The cell line according to item 27, wherein the cell line contains an expression vector according to item 26.

---

The invention claimed is:

1. A monoclonal antibody that specifically binds to human GDF-15, or an antigen-binding portion thereof, comprising a heavy chain variable domain and a light chain variable domain, wherein: the heavy chain variable domain comprises the heavy chain CDR1, CDR2 and CDR3 amino acid sequences of antibody B1-23; and the light chain variable domain comprises the light chain CDR1, CDR2 and CDR3 amino acid sequences of antibody B1-23.

2. The monoclonal antibody or antigen-binding portion thereof of claim 1, wherein: the heavy chain variable domain comprises the CDR1, CDR2 and CDR3 amino acid sequences of SEQ ID Nos: 3, 4, and 5, respectively; and the light chain variable domain comprises the CDR1, CDR2 and CDR3 amino acid sequences of SEQ ID NO. 6, SAS, and SEQ ID NO. 7, respectively.

3. The monoclonal antibody or antigen-binding portion thereof of claim 2, which is a humanized antibody.

4. A monoclonal antibody that specifically binds to human GDF-15, or an antigen-binding portion thereof, comprising a heavy chain variable domain comprising the amino acid sequence of the heavy chain variable domain of antibody B1-23.

5. The monoclonal antibody or antigen-binding portion thereof of claim 4, further comprising a light chain variable domain comprising the amino acid sequence of the light chain variable domain of antibody B1-23.

6. A monoclonal antibody that specifically binds to human GDF-15, or an antigen-binding portion thereof, comprising a light chain variable domain comprising the amino acid sequence of the light chain variable domain of antibody B1-23.

7. The monoclonal antibody or an antigen-binding portion thereof of claim 5, which is antibody B1-23 or an antigen-binding portion thereof.

8. A pharmaceutical composition comprising the antibody or antigen-binding portion thereof of claim 2.

9. A nucleotide sequence encoding the heavy chain variable domain and/or the light chain variable domain of the monoclonal antibody or antigen-binding portion thereof of claim 2.

10. An expression vector comprising the nucleotide sequence of claim 9.

11. A cell line capable of producing an antibody or antigen-binding portion thereof of claim 2.

12. The cell line of claim 11, which is the hybridoma cell line B1-23.

13. A monoclonal antibody that specifically binds to human GDF-15, or an antigen-binding portion thereof, comprising a heavy chain comprising the amino acid sequence of the heavy chain of antibody B1-23.

14. A monoclonal antibody that specifically binds to human GDF-15, or an antigen-binding portion thereof, comprising a light chain comprising the amino acid sequence of the light chain of antibody B1-23.

15. A pharmaceutical composition comprising the antibody or antigen-binding portion thereof of claim 1.

16. A nucleotide sequence encoding the heavy chain variable domain and/or the light chain variable domain of the monoclonal antibody or antigen-binding portion thereof of claim 1.

17. An expression vector comprising the nucleotide sequence of claim 16.

18. A method of inhibiting GDF-15 mediated downregulation of Natural Killer Group 2D (NKG2D) receptor on Natural Killer (NK) cells in a cell culture, the method comprising administering to the cell culture the monoclonal antibody or antigen-binding portion thereof of claim 1.

19. A method of inhibiting GDF-15 mediated downregulation of Natural Killer Group 2D (NKG2D) receptor on Natural Killer (NK) cells in a cell culture, the method comprising administering to the cell culture the monoclonal antibody or antigen-binding portion thereof of claim 2.

20. A method of inhibiting GDF-15 mediated downregulation of Natural Killer Group 2D (NKG2D) receptor on Natural Killer (NK) cells in a mammal, the method comprising administering to the mammal the monoclonal antibody or antigen-binding portion thereof of claim 2.

* * * * *